US010500053B2

(12) United States Patent
Hollister et al.

(10) Patent No.: US 10,500,053 B2
(45) Date of Patent: Dec. 10, 2019

(54) MODULAR TISSUE SCAFFOLDS

(71) Applicant: DePuy Synthes Products, Inc., Raynham, MA (US)

(72) Inventors: Scott J. Hollister, Atlanta, GA (US); Stephen E. Feinberg, Ann Arbor, MI (US); William L. Murphy, Waunakee, WI (US); Leenaporn Jongpaiboonkit, Madison, WI (US); James R. Adox, Ann Arbor, MI (US); Francesco Migneco, Ypsilanti, MI (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/935,404

(22) Filed: Mar. 26, 2018

(65) Prior Publication Data

US 2019/0000628 A1 Jan. 3, 2019

Related U.S. Application Data

(63) Continuation of application No. 13/407,441, filed on Feb. 28, 2012, now Pat. No. 9,943,410.

(Continued)

(51) Int. Cl.
*A61F 2/28* (2006.01)
*B33Y 80/00* (2015.01)
*A61F 2/30* (2006.01)

(52) U.S. Cl.
CPC ............. *A61F 2/28* (2013.01); *A61F 2/2803* (2013.01); *A61F 2/2875* (2013.01);
(Continued)

(58) Field of Classification Search
CPC ........ A61F 2/28; A61F 2/2803; A61F 2/2846; A61F 2/2875; A61F 2002/28; A61F 2002/2803; A61F 2002/2807; A61F 2002/281; A61F 2002/2825; A61F 2002/2835; A61F 2002/2839; A61F 2002/2846; A61F 2002/285;
(Continued)

(56) References Cited

U.S. PATENT DOCUMENTS 3,488,779 A * 1/1970 Christensen ....... A61B 17/8071
606/71
3,683,422 A * 8/1972 Stemmer ............... A61F 2/2803
623/23.51

(Continued)

FOREIGN PATENT DOCUMENTS

DE 3933459 A1 4/1991
WO 2002/071921 A2 9/2002
WO 2011/010463 A1 1/2011

OTHER PUBLICATIONS

Wu, Arming antibodies: prospects and challenges for immunoconjugates. Nature biotechnology. Sep. 2005;23(9):1137.

(Continued)

*Primary Examiner* — Lynnsy M Summitt
(74) *Attorney, Agent, or Firm* — BakerHostetler

(57) ABSTRACT

Provided are biocompatible and implantable scaffolds for treating a tissue defect, such as a bone gap. The scaffolds can have a modular design comprising a tissue scaffold rack designed to accommodate one or more modules. Also provided are methods for fabrication and use of such scaffolds.

24 Claims, 10 Drawing Sheets

Related U.S. Application Data

(60) Provisional application No. 61/447,352, filed on Feb. 28, 2011.

(52) U.S. Cl.
CPC ............... *A61F 2002/305* (2013.01); *A61F 2002/30062* (2013.01); *A61F 2002/30331* (2013.01); *A61F 2002/30387* (2013.01); *A61F 2002/30457* (2013.01); *A61F 2002/30604* (2013.01); *A61F 2002/30677* (2013.01); *A61F 2002/30948* (2013.01); *A61F 2002/30952* (2013.01); *A61F 2002/30962* (2013.01); *B33Y 80/00* (2014.12)

(58) Field of Classification Search
CPC ...... A61F 2002/2853; A61F 2002/2871; A61F 2002/2889; A61F 2002/2892; A61F 2002/2896; A61F 2002/2882
See application file for complete search history.

(56) References Cited

U.S. PATENT DOCUMENTS

| | | | | |
|---|---|---|---|---|
| 3,710,789 A * | 1/1973 | Ersek | ............... | A61B 17/8085 606/281 |
| 3,720,959 A * | 3/1973 | Hahn | ............... | A61F 2/2803 623/17.17 |
| 3,849,805 A * | 11/1974 | Leake | ............... | A61F 2/2803 623/17.17 |
| 4,222,128 A * | 9/1980 | Tomonaga | ......... | A61C 8/0012 106/35 |
| 4,297,164 A | 10/1981 | Lee | | |
| 4,309,778 A | 1/1982 | Buechel et al. | | |
| 4,344,191 A * | 8/1982 | Wagner | ............... | A61F 2/2803 623/17.18 |
| 4,365,356 A * | 12/1982 | Broemer | ............ | A61F 2/30767 623/23.51 |
| 4,512,038 A * | 4/1985 | Alexander | ............ | A61B 17/80 606/281 |
| 4,553,272 A * | 11/1985 | Mears | ............... | A61F 2/30 623/1.4 |
| 4,636,215 A * | 1/1987 | Schwartz | ............ | A61F 2/2803 606/76 |
| 4,684,370 A * | 8/1987 | Barrett | ............... | A61C 8/00 433/229 |
| 4,693,722 A * | 9/1987 | Wall | ............... | A61F 2/30965 623/17.17 |
| 4,778,472 A * | 10/1988 | Homsy | ............ | A61F 2/30965 623/17.17 |
| 4,787,906 A * | 11/1988 | Haris | ............... | A61F 2/2803 433/201.1 |
| 4,863,472 A * | 9/1989 | Tormala | ............ | A61C 8/00 623/23.58 |
| 4,865,607 A | 9/1989 | Witzel et al. | | |
| 4,888,018 A * | 12/1989 | Giampapa | ............ | A61F 2/2803 128/898 |
| 4,950,296 A * | 8/1990 | McIntyre | ............ | A61F 2/28 606/76 |
| 5,032,445 A * | 7/1991 | Scantlebury | ......... | A61C 8/0006 106/35 |
| 5,084,051 A * | 1/1992 | Tormala | ............... | A61L 31/129 428/688 |
| 5,087,259 A * | 2/1992 | Krenkel | ............ | A61B 17/8071 606/60 |
| 5,108,437 A * | 4/1992 | Kenna | ............... | A61F 2/3672 623/16.11 |
| 5,133,755 A * | 7/1992 | Brekke | ............... | A61F 2/28 623/23.51 |
| 5,152,791 A * | 10/1992 | Hakamatsuka | ......... | A61F 2/28 623/23.56 |
| 5,195,951 A * | 3/1993 | Giampapa | ............ | A61F 2/2803 623/17.17 |
| 5,211,664 A * | 5/1993 | Tepic | ............... | A61F 2/2846 606/60 |
| 5,298,254 A * | 3/1994 | Prewett | ............... | A61B 17/686 424/422 |
| 5,314,478 A * | 5/1994 | Oka | ............... | A61F 2/28 623/14.12 |
| 5,380,328 A * | 1/1995 | Morgan | ............ | A61B 17/8071 606/70 |
| 5,443,483 A * | 8/1995 | Kirsch | ............... | A61B 17/80 600/37 |
| 5,466,262 A * | 11/1995 | Saffran | ............... | A61B 17/80 606/74 |
| 5,489,305 A * | 2/1996 | Morgan | ............ | A61B 17/8071 623/17.17 |
| 5,496,371 A * | 3/1996 | Eppley | ............... | A61F 2/2803 623/17.18 |
| 5,496,372 A * | 3/1996 | Hamamoto | ......... | A61C 8/0012 606/298 |
| 5,514,179 A * | 5/1996 | Brennan | ............... | A61F 2/0059 623/17.18 |
| 5,554,194 A * | 9/1996 | Sanders | ............... | A61F 2/2803 403/141 |
| 5,569,308 A * | 10/1996 | Sottosanti | ............... | A61F 2/28 424/422 |
| 5,580,247 A * | 12/1996 | Gittleman | ............ | A61B 17/6433 433/173 |
| 5,591,234 A * | 1/1997 | Kirsch | ............... | A61B 17/80 606/70 |
| 5,607,474 A * | 3/1997 | Athanasiou | ............ | A61F 2/28 623/23.71 |
| 5,653,760 A * | 8/1997 | Saffran | ............... | A61B 17/80 606/154 |
| 5,676,699 A * | 10/1997 | Gogolewski | ............ | C08L 89/00 623/16.11 |
| 5,728,157 A * | 3/1998 | Prescott | ............... | A61B 17/0057 424/423 |
| 5,730,743 A * | 3/1998 | Kirsch | ............... | A61B 17/8085 606/215 |
| 5,741,257 A * | 4/1998 | Kirsch | ............... | A61B 17/80 606/215 |
| 5,769,637 A * | 6/1998 | Morgan | ............ | A61B 17/8071 433/176 |
| 5,769,897 A * | 6/1998 | Harle | ............... | A61F 2/0095 424/423 |
| 5,807,406 A * | 9/1998 | Brauker | ............... | A61F 2/00 424/422 |
| 5,824,088 A * | 10/1998 | Kirsch | ............... | A61B 17/80 424/423 |
| 5,863,297 A * | 1/1999 | Walter | ............... | A61F 2/28 264/219 |
| 5,876,452 A * | 3/1999 | Athanasiou | ............ | A61F 2/28 424/424 |
| 5,885,829 A * | 3/1999 | Mooney | ............ | A61L 27/3604 424/422 |
| 5,899,939 A * | 5/1999 | Boyce | ............... | A61F 2/28 523/113 |
| 5,919,234 A * | 7/1999 | Lemperle | ............ | A61B 17/688 128/898 |
| 5,948,020 A * | 9/1999 | Yoon | ............... | A61L 31/06 600/37 |
| 5,954,769 A * | 9/1999 | Rosenlicht | ......... | A61B 17/1739 433/173 |
| 5,989,292 A * | 11/1999 | van Loon | ............ | A61F 2/3099 623/17.17 |
| 6,013,853 A * | 1/2000 | Athanasiou | ............ | A61F 2/0811 424/423 |
| 6,025,538 A * | 2/2000 | Yaccarino, III | ............ | A61F 2/28 128/898 |
| 6,060,641 A * | 5/2000 | Manolidis | ............ | A61F 2/2803 128/898 |
| 6,093,201 A * | 7/2000 | Cooper | ............... | A61B 17/80 606/232 |
| 6,123,731 A * | 9/2000 | Boyce | ............... | A61B 17/7062 523/113 |
| 6,200,347 B1 * | 3/2001 | Anderson | ............ | A61F 2/28 623/16.11 |

(56) References Cited

U.S. PATENT DOCUMENTS

| | | | | |
|---|---|---|---|---|
| 6,254,639 B1* | 7/2001 | Peckitt | A61B 17/80 | 623/11.11 |
| 6,283,997 B1* | 9/2001 | Garg | A61F 2/28 | 623/16.11 |
| 6,299,649 B1* | 10/2001 | Chang | A61F 2/30942 | 623/23.34 |
| 6,325,803 B1* | 12/2001 | Schumacher | A61B 17/8047 | 606/104 |
| 6,328,765 B1* | 12/2001 | Hardwick | A61F 2/2803 | 623/23.58 |
| 6,350,284 B1* | 2/2002 | Tormala | A61F 2/2846 | 623/16.11 |
| 6,376,573 B1* | 4/2002 | White | A61F 2/28 | 523/115 |
| 6,391,059 B1* | 5/2002 | Lemperle | A61B 17/688 | 606/151 |
| 6,398,811 B1* | 6/2002 | McKay | A61F 2/446 | 623/16.11 |
| 6,409,764 B1* | 6/2002 | White | A61C 8/0006 | 424/424 |
| 6,440,444 B2* | 8/2002 | Boyce | A61F 2/28 | 424/422 |
| 6,474,901 B1 | 11/2002 | Thurston | | |
| 6,616,698 B2* | 9/2003 | Scarborough | A61L 27/3608 | 623/23.51 |
| 6,626,950 B2* | 9/2003 | Brown | A61F 2/30749 | 623/23.72 |
| 6,632,247 B2* | 10/2003 | Boyer, II | B29C 43/006 | 623/23.6 |
| 6,635,087 B2* | 10/2003 | Angelucci | A61B 17/7059 | 606/249 |
| 6,645,250 B2* | 11/2003 | Schulter | A61C 8/0006 | 433/199.1 |
| 6,652,592 B1* | 11/2003 | Grooms | A61F 2/08 | 606/60 |
| 6,696,073 B2* | 2/2004 | Boyce | A61B 17/0401 | 424/422 |
| 6,712,851 B1* | 3/2004 | Lemperle | A61B 17/688 | 606/151 |
| 6,758,862 B2* | 7/2004 | Berry | A61F 2/44 | 606/247 |
| 6,761,738 B1* | 7/2004 | Boyd | A61F 2/28 | 623/17.11 |
| 6,761,739 B2* | 7/2004 | Shepard | A61F 2/28 | 623/16.11 |
| 6,776,800 B2* | 8/2004 | Boyer, II | A61B 17/0401 | 623/16.11 |
| 6,821,279 B2* | 11/2004 | Di Emidio | A61B 17/8071 | 606/285 |
| 6,887,272 B2* | 5/2005 | Shinomiya | A61L 27/46 | 623/16.11 |
| 6,902,578 B1* | 6/2005 | Anderson | A61F 2/28 | 623/16.11 |
| 6,979,353 B2* | 12/2005 | Bresina | A61B 17/1637 | 623/17.11 |
| 6,989,033 B1* | 1/2006 | Schmidt | A61F 2/44 | 623/23.51 |
| 7,019,192 B2* | 3/2006 | Gertzman | C08L 5/08 | 623/16.11 |
| 7,037,339 B2* | 5/2006 | Houfburg | A61F 2/4455 | 623/17.11 |
| 7,037,867 B2* | 5/2006 | Yu | A61L 27/12 | 501/1 |
| 7,087,082 B2* | 8/2006 | Paul | A61F 2/28 | 623/16.11 |
| 7,122,057 B2* | 10/2006 | Beam | A61L 27/12 | 623/23.51 |
| 7,131,995 B2* | 11/2006 | Biedermann | A61F 2/2846 | 623/23.46 |
| 7,174,282 B2 | 2/2007 | Hollister et al. | | |
| 7,208,222 B2* | 4/2007 | Rolfe | A61B 17/8605 | 428/131 |
| 7,252,685 B2* | 8/2007 | Bindseil | A61F 2/4455 | 427/2.26 |
| 7,297,164 B2 | 11/2007 | Johnson et al. | | |
| 7,300,465 B2* | 11/2007 | Paul | A61F 2/28 | 623/17.11 |
| 7,309,361 B2 | 12/2007 | Wasielewski | | |
| 7,335,232 B2* | 2/2008 | Pointillart | A61F 2/2846 | 606/250 |
| 7,453,263 B2 | 11/2008 | Kim et al. | | |
| 7,455,695 B2 | 11/2008 | Khalili et al. | | |
| 7,468,078 B2 | 12/2008 | Sederholm et al. | | |
| 7,476,255 B2 | 1/2009 | Lester et al. | | |
| 7,481,841 B2 | 1/2009 | Hazebrouck et al. | | |
| 7,534,451 B2* | 5/2009 | Erbe | A61B 17/80 | 424/422 |
| 7,537,617 B2* | 5/2009 | Bindsell | A61F 2/28 | 623/17.11 |
| 7,563,274 B2 | 7/2009 | Justis et al. | | |
| 7,601,173 B2* | 10/2009 | Messerli | A61F 2/28 | 606/246 |
| 7,731,756 B2* | 6/2010 | Maspero | A61L 27/3847 | 433/201.1 |
| 7,887,587 B2* | 2/2011 | Griffiths | A61L 31/16 | 623/16.11 |
| 7,934,928 B2* | 5/2011 | Nishida | A61C 8/0083 | 433/173 |
| 7,972,616 B2* | 7/2011 | Dubrow | A61F 13/02 | 424/423 |
| 7,985,231 B2* | 7/2011 | Sankaran | A61F 2/4455 | 606/105 |
| 8,114,841 B2* | 2/2012 | Lynch | A61L 27/12 | 424/484 |
| 8,182,532 B2 | 5/2012 | Anderson et al. | | |
| 8,206,450 B2* | 6/2012 | Henry | A61L 27/48 | 623/17.17 |
| 8,221,500 B2* | 7/2012 | Truncale | A61F 2/28 | 623/16.11 |
| 8,231,685 B2* | 7/2012 | Fritz | C12N 5/0655 | 623/23.57 |
| 8,241,298 B2* | 8/2012 | Sengun | A61F 2/4618 | 606/108 |
| 8,262,734 B2* | 9/2012 | Dewey | A61F 2/44 | 606/90 |
| 8,303,976 B2* | 11/2012 | Sapieszko | A61F 2/28 | 424/422 |
| 8,353,967 B2* | 1/2013 | Malmquist | A61F 2/2803 | 424/423 |
| 8,366,786 B2* | 2/2013 | Shoji | A61F 2/28 | 623/16.11 |
| 8,398,714 B2* | 3/2013 | Boiangiu | A61F 2/02 | 623/16.11 |
| 8,414,654 B1* | 4/2013 | Ganey | A61F 2/28 | 623/16.11 |
| 8,431,147 B2* | 4/2013 | Drapeau | A61L 27/20 | 424/423 |
| 8,444,699 B2* | 5/2013 | Metzger | A61F 2/28 | 623/23.46 |
| 8,460,686 B2* | 6/2013 | Clineff | A61L 27/10 | 424/400 |
| 8,485,820 B1* | 7/2013 | Ali | A61C 8/0027 | 433/173 |
| 8,518,123 B2* | 8/2013 | Jensen | A61L 27/44 | 623/23.51 |
| 9,398,960 B2* | 7/2016 | Rosen | A61F 2/4455 | |
| 2001/0018614 A1* | 8/2001 | Bianchi | A61F 2/28 | 623/16.11 |
| 2001/0039455 A1* | 11/2001 | Simon | A61B 17/1604 | 623/23.51 |
| 2002/0029084 A1 | 3/2002 | Paul et al. | | |
| 2002/0032483 A1 | 3/2002 | Nicholson et al. | | |
| 2002/0035401 A1* | 3/2002 | Boyce | A61F 2/28 | 623/23.51 |
| 2002/0082779 A1* | 6/2002 | Ascenzi | G09B 23/30 | 702/19 |
| 2003/0009235 A1* | 1/2003 | Manrique | A61B 17/866 | 623/23.63 |

(56) References Cited

U.S. PATENT DOCUMENTS

| | | | |
|---|---|---|---|
| 2003/0060892 A1* | 3/2003 | Richter | A61F 2/28 623/23.51 |
| 2003/0069718 A1 | 4/2003 | Hollister et al. | |
| 2003/0074064 A1* | 4/2003 | Gerbec | A61F 2/4455 623/16.11 |
| 2003/0171812 A1 | 9/2003 | Grunberg et al. | |
| 2003/0185870 A1* | 10/2003 | Grinstaff | A61L 27/227 424/423 |
| 2004/0024466 A1* | 2/2004 | Heerklotz | A61C 8/0006 623/17.17 |
| 2004/0030338 A1 | 2/2004 | Paul | |
| 2004/0030342 A1 | 2/2004 | Trieu et al. | |
| 2004/0193268 A1 | 9/2004 | Hazebrouck | |
| 2004/0249464 A1* | 12/2004 | Bindseil | A61F 2/4455 623/17.16 |
| 2005/0033427 A1* | 2/2005 | Freilich | A61B 17/68 623/16.11 |
| 2005/0085914 A1* | 4/2005 | Lange | A61F 2/4465 623/17.11 |
| 2005/0107880 A1* | 5/2005 | Shimp | A61F 2/28 623/17.11 |
| 2005/0113930 A1* | 5/2005 | Ganz | A61C 8/0006 623/17.17 |
| 2005/0159754 A1* | 7/2005 | Odrich | A61B 17/66 606/86 R |
| 2005/0177245 A1* | 8/2005 | Leatherbury | A61B 17/7059 623/23.5 |
| 2005/0261780 A1* | 11/2005 | Heino | A61B 17/8085 623/23.51 |
| 2005/0267482 A1* | 12/2005 | Hyde, Jr. | A61B 17/1637 606/79 |
| 2006/0058880 A1 | 3/2006 | Wysocki et al. | |
| 2006/0089646 A1* | 4/2006 | Bonutti | A61B 17/0218 606/279 |
| 2006/0149385 A1 | 7/2006 | McKay | |
| 2006/0195179 A1* | 8/2006 | Sun | A61L 27/38 623/1.54 |
| 2006/0200235 A1 | 9/2006 | Bianchi et al. | |
| 2006/0246103 A1* | 11/2006 | Ralph | A61K 9/0024 424/422 |
| 2006/0265077 A1* | 11/2006 | Zwirkoski | A61B 17/7094 623/17.16 |
| 2006/0276925 A1 | 12/2006 | Lin et al. | |
| 2007/0179610 A1* | 8/2007 | Biedermann | A61F 2/44 623/16.11 |
| 2007/0276489 A1* | 11/2007 | Bindseil | A61F 2/4455 623/16.11 |
| 2008/0027453 A1* | 1/2008 | Johnson | A61B 17/025 606/90 |
| 2008/0039845 A1* | 2/2008 | Bonutti | A61B 17/0401 606/62 |
| 2008/0051868 A1 | 2/2008 | Cottone et al. | |
| 2008/0091201 A1 | 4/2008 | Reiley | |
| 2008/0195211 A1 | 8/2008 | Lin et al. | |
| 2008/0215093 A1 | 9/2008 | Lin et al. | |
| 2008/0228278 A1* | 9/2008 | Lee | A61C 8/001 623/17.17 |
| 2008/0288083 A1* | 11/2008 | Axelsson | A61F 2/30907 623/23.51 |
| 2009/0062821 A1* | 3/2009 | Johnson | A61F 2/30756 606/151 |
| 2009/0112332 A1* | 4/2009 | Shelokov | A61F 2/30907 623/23.72 |
| 2009/0138086 A1 | 5/2009 | Dewey | |
| 2009/0155334 A1* | 6/2009 | Mallick | A61L 27/3834 424/423 |
| 2009/0187245 A1* | 7/2009 | Steiner | A61F 2/4455 623/16.11 |
| 2009/0198337 A1 | 8/2009 | Phan | |
| 2009/0214652 A1* | 8/2009 | Hunter | A61K 38/17 424/486 |
| 2009/0216232 A1 | 8/2009 | Buford et al. | |
| 2009/0291112 A1* | 11/2009 | Truncale | A61F 2/28 424/423 |
| 2010/0112028 A1* | 5/2010 | Hellerbrand | A61L 27/26 514/1.1 |
| 2010/0137990 A1* | 6/2010 | Apatsidis | A61B 17/866 623/17.16 |
| 2010/0161061 A1* | 6/2010 | Hunt | A61F 2/28 623/17.16 |
| 2010/0168771 A1* | 7/2010 | Guldberg | A61L 27/3804 606/151 |
| 2010/0168798 A1* | 7/2010 | Clineff | A61L 27/54 606/279 |
| 2010/0266660 A1* | 10/2010 | McKay | A61B 17/707 424/426 |
| 2010/0268349 A1* | 10/2010 | Bianchi | A61L 2/025 623/23.51 |
| 2010/0332248 A1* | 12/2010 | Pettersson | G06F 19/321 705/2 |
| 2011/0060558 A1* | 3/2011 | Pettersson | A61B 17/8685 703/1 |
| 2011/0137417 A1* | 6/2011 | Lee | A61F 2/4455 623/16.11 |
| 2011/0172826 A1* | 7/2011 | Amodei | A61K 9/0024 700/266 |
| 2011/0202142 A1* | 8/2011 | Mao | A61L 27/3817 623/23.72 |
| 2011/0282392 A1 | 11/2011 | Murphy et al. | |
| 2012/0089238 A1* | 4/2012 | Kang | B29C 64/112 623/23.72 |
| 2012/0107407 A1* | 5/2012 | Armbruster | A61L 27/46 424/491 |
| 2012/0123542 A1* | 5/2012 | Suzuki | A61F 2/28 623/16.11 |
| 2012/0136441 A1* | 5/2012 | Yang | A61L 27/446 623/17.11 |
| 2013/0018480 A1* | 1/2013 | Kopp | A61L 27/047 623/23.5 |
| 2013/0030472 A1* | 1/2013 | Williams | A61B 17/70 606/279 |
| 2013/0211540 A1* | 8/2013 | Tate | A61B 17/56 623/23.57 |
| 2013/0218282 A1* | 8/2013 | Hunt | A61F 2/30 623/19.11 |

OTHER PUBLICATIONS

Wagner et al., "The Crossflow injection technique: An Improvement of the ethanol injection method", J. Liposome Res, 2002, pp. 259-270, vol. 12, No. 3.

Varde et al., Microspheres for controlled release drug delivery, 2004, Expert Opin. Biol. 4(1) 35-51.

Stayton et al, Smart'delivery systems for biomolecular therapeutics. Orthodontics & craniofacial research. Aug. 2005 1;8(3):219-225.

Murphy etal., "Effects of a bone-like mineral film on phenotype of adult human mesenchymal stem cells in vitro", Biomaterials 26:303-10, 2005.

Murphy etal., "Bioinspired growth of crystalline carbonate apatite on biodegradable polymer substrata", J Am Chem Soc 124:1910-7, 2002.

Minuth et al. (2005) Tissue Engineering: From Cell Biology to Artificial Organs, John Wiley & Sons, ISBN 3527311866.

Lin et al. "A novel method for internal architecture design to match bone elastic properties with desired porosity", Journal of Biomechanics 37:623-36, 2004.

International Search Report and Written Opinion dated Jun. 22, 2012 in related PCT Application No. PCT/US2012/026996 filed Feb. 28, 2012, 9 pages.

Hollister, S.J. Scaffold engineering: a bridge to where? Biofabrication 1(1) :012001 (2009).

Rengel et al., High efficiency entrapment of superoxide dismutase into mucoadhesive chitosan-coated liposomes, (2002) Eur. J. Pharm. Sci. 15, 441-448.

\* cited by examiner

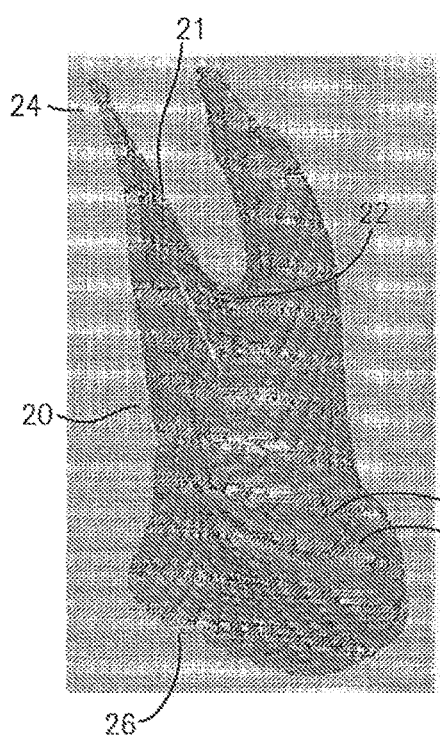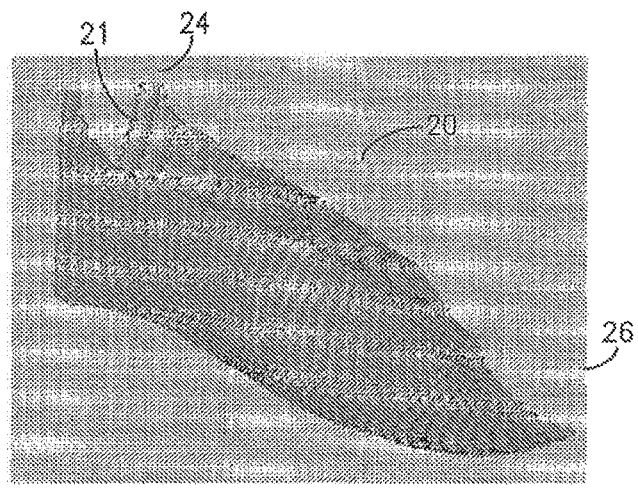
FIG. 1A
FIG. 1B

MODULAR TISSUE SCAFFOLDS

CROSS-REFERENCE TO RELATED APPLICATIONS

The present application is a continuation of U.S. application Ser. No. 13/407,441, filed on Feb. 28, 2012, now U.S. Pat. No. 9,943,410, which claims the benefit of priority to U.S. Provisional Application Ser. No. 61/447,352 filed 28 Feb. 2011, each of which is hereby incorporated by reference in its entirety.

FIELD OF THE INVENTION

The present disclosure generally relates to tissue scaffolds. More specifically, degradable tissue scaffolds are provided having modules for filling a gap in a tissue, where a variable number of modules are inserted into the scaffold as needed to fill the gap.

BACKGROUND OF THE INVENTION

Extensive research has been devoted to the development of degradable tissue scaffolds to fill bone, cartilage or soft tissue defects (Hollister, 2009). The scaffolds that have been developed are generally custom designed and prepared for a defect in a particular individual, are prepared in standardized sizes, or are initially flowable so the scaffold can be injected to fill the tissue gap. For defects that are variable in size, for example a defect in a mandible or long bone due to tumor resection or injury, the scaffolds must be custom designed to fit the defect. This is an expensive, time consuming process that can preclude the use of scaffolds in favor of more traditional approaches such as the grafting of free flap autografts.

Modular orthopaedic implants that can be expanded have been described (see e.g., U.S. Pat. No. 7,481,841, describing a metal prosthesis that may be adjusted via a radio signal; U.S. Pat. No. 7,468,078, describing a modular hip prosthesis with different ball and stem; U.S. Pat. No. 7,455,695, describing a femoral stem modular prosthesis with interlocking nut; U.S. Pat. No. 7,453,263, describing a modular femoral head and neck prosthesis; U.S. Pat. No. 7,309,361, describing a coupled metallic tibia and femoral implant with resorbable lining; and U.S. Pat. No. 7,297,164, describing a modular knee prosthesis with tibial and femoral components broken into medial and lateral sides. But such modular orthopaedic implants have generally been made from permanent materials, or at most a combination of a permanent material with a degradable liner (see e.g., U.S. Pat. No. 7,309,361). Furthermore, permanent materials of conventional modular implants do not provide for surface release of biologic factors individually or separately from one or more individual modules.

While permanent materials have a long history of clinical use, they also have significant drawbacks. Firstly, they are radiopaque, which makes evaluating the degree of healing post-operatively difficult. Secondly, there is a large difference between the elastic modulus of the metal implant and that of the adjacent bone. This can cause stress shielding, which in turn can lead to complications including: implant/screw loosening, future instrumentation failure, device-related osteopenia, soft tissue dehiscence, and fracture. Finally, micromotion of the metal device can create wear debris that triggers an inflammatory response. More recently, devices have been composed from non-degradable polymers, most notably polyether-etherketone (PEEK). While these devices do have the advantage of being radiolucent, the mismatch between the modulus of the material and the bone as well as the potential for wear debris still exist.

SUMMARY OF THE INVENTION

Among the various aspects of the present disclosure is the provision of a tissue scaffold comprising a first module that is biocompatible and degradable when implanted into a vertebrate, long bone, mandible or cranium, wherein the first module is designed to couple to a second module that is biocompatible and degradable when implanted into a mammal, and wherein the first module comprises an A connector designed to couple to a B connector present on the second module.

In another embodiment of a biocompatible system for filling a tissue gap, the system comprises a first tissue scaffold module that is biocompatible and degradable when implanted into a vertebrate, wherein the first tissue scaffold module is designed to couple to a second tissue scaffold module that is biocompatible and degradable when implanted into the vertebrate, additional tissue scaffold modules as needed to fill the tissue gap when joined to the first tissue scaffold module, the second tissue scaffold module, or one of the additional tissue scaffold modules, and a biocompatible rack designed to accommodate the first tissue scaffold module, the second tissue scaffold module and the additional tissue scaffold modules.

In another embodiment of a biocompatible system for filling a gap in a long bone of a mammal, the system comprises at least one tissue scaffold module that is degradable when implanted in the mammal, wherein each module has an irregular disk shape having two flat sides and each module comprises a dovetail connector on each flat side, wherein the dovetail connector from one module is designed to couple with a dovetail connector from another module and wherein the circumference of the irregular disk shape is substantially in the form of an outline of missing tissue in the gap in the long bone, and a biocompatible rack comprising a trough shaped portion having two side regions, a bottom region, a proximal end and distal end, wherein the modules fit into the trough shaped region by contacting the bottom region and substantially spanning the two side regions, wherein each module and the rack have a porous microstructure, are synthesized from polycaprolactone and are substantially coated with calcium-deficient carbonate-containing hydroxyapatite, and wherein the system comprises a sufficient number of modules to substantially fill the gap.

In another embodiment of a biocompatible system for filling a gap in a mandible of a mammal, the system comprises at least one tissue scaffold module that is degradable when implanted in the mammal, wherein each module has an irregular disk shape having two flat sides and each module comprises a dovetail connector on each flat side, wherein the dovetail connector from one module is designed to couple with a dovetail connector from another module and wherein the circumference of the irregular disk shape is substantially in the form of an outline of missing tissue in the gap in the mandible, a biocompatible rack comprising a trough shaped portion having two side regions, a bottom region, a proximal end and distal end, wherein the modules fit into the trough shaped region by contacting the bottom region and substantially spanning the two side regions, wherein the rack spans the mandible gap by the ends of the trough shaped region partially enveloping the mandible, wherein each module and the rack have a porous microstructure, are synthesized from polycaprolactone and are substantially coated with calcium-deficient carbonate-containing hydroxyapatite, and wherein the system comprises a sufficient number of modules to substantially fill the gap.

In one or more embodiments the tissue scaffold further comprises a second module, wherein the second module is joined to the first module by coupling the B connector of the second module to the A connector of the first module. In another embodiment the A connector is integral to the first module and the B connector is integral to the second module. In some embodiments the A connector is identical to the B connector. In some embodiments the A connector is not identical to the B connector. In some embodiments the A connector and B connector are dovetail connectors. In some embodiments the dovetail connectors are elliptical. In some embodiments the first module and second module comprise both an A connector and a B connector.

In some embodiments, the tissue scaffold further comprises a third module that is biocompatible and degradable, wherein the third module comprises both an A connector and a B connector and is joined to the first module or the second module by the third module A connector or B connector. In some embodiments the first module and second module each have an irregular disk shape having two flat sides, wherein the A connector is on one flat side and the B connector is on the other flat side, and wherein the circumference of the irregular disk shape is substantially in the form of an outline of missing tissue of a tissue gap. In some embodiments the first module and second module each have an irregular disk shape having two flat sides, the first module comprises an A connector on one flat side and an A connector on the other flat side, the second module comprises a B connector on one flat side and a B connector on the other flat side, and the circumference of the irregular disk shape is substantially in the form of an outline of missing tissue of a tissue gap.

In some embodiments the first module and the second module comprise a bioactive agent or a vertebrate cell, wherein the bioactive agent or vertebrate cell in the first module is different from the bioactive agent or vertebrate cell in the second module. In some embodiments the first module and second module both have a porous microstructure. In some embodiments the first module and second module are synthesized from a material independently selected from a degradable polymer and a mixture of a degradable polymer and a bioceramic. In some embodiments the polymer is polycaprolactone, polylactide, polyglycolide, poly(lactide-glycolide), poly(propylene fumarate), poly(caprolactone fumarate), polyethylene glycol, poly(glycolide-co-caprolactone), or mixtures thereof. In some embodiments the polymer is polycaprolactone.

In some embodiments the first module and/or the second module further comprise a ridge designed to be melted by the application of energy, wherein the application of energy to the ridge fuses the first module to the second module. In some embodiments the ridge is on the A connector and/or on the B connector. In some embodiments the first module comprises an osteoconductive mineral coating on at least a portion of the module. In some embodiments the osteoconductive mineral coating is hydroxyapatite, calcium-deficient carbonate-containing hydroxyapatite, tricalcium phosphate, amorphous calcium phosphate, octacalcium phosphate, dicalcium phosphate, calcium phosphate, or a mixture thereof. In some embodiments the osteoconductive mineral coating is calcium-deficient carbonate-containing hydroxyapatite.

In some embodiments the tissue scaffold comprises a bioactive agent. In some embodiments the bioactive agent is with the first module. In some embodiments the bioactive agent is present in an amount that induces ossification. In some embodiments the bioactive agent is a bone morphogenetic protein (BMP), demineralized bone matrix, a bone marrow aspirate, a transforming growth factor, a fibroblast growth factor, an insulin-like growth factor, a platelet derived growth factor, a vascular endothelial growth factor, a growth and development factor-5, platelet rich plasma, or a mixture thereof. In some embodiments the bioactive agent is BMP2 or BMP7.

In some embodiments the tissue scaffold comprises a vertebrate cell. In some embodiments the vertebrate cell is a mammalian cell. In some embodiments the vertebrate cell is with the first module. In some embodiments the vertebrate cell is a stem cell. In some embodiments the stem cell is an embryonic stem cell. In some embodiments the stem cell is an adult stem cell. In some embodiments the stem cell is a mesenchymal stem cell or an induced pluripotent stem cell.

In some embodiments the A connector is identical to the B connector, the first module has a porous microstructure, the first module is synthesized from polycaprolactone, and the first module is substantially coated with calcium-deficient carbonate-containing hydroxyapatite.

In some embodiments the tissue scaffold further comprises a tissue scaffold rack designed to accommodate the first module and the second module, wherein the first module and second module are joined to the tissue scaffold rack. In some embodiments the tissue scaffold is designed to span a tissue gap in the vertebrate. In some embodiments the rack is degradable when implanted into a mammal.

In some embodiments the rack has a porous microstructure, the rack is synthesized from polycaprolactone, and the rack is substantially coated with calcium-deficient carbonate-containing hydroxyapatite. In some embodiments the first module and/or the second module and/or the rack further comprise a ridge designed to be melted by the application of energy, wherein the application of energy to the ridge fuses the first module and/or the second module to the rack, and/or the first module to the second module. In some embodiments each module further comprises a C connector that can couple to a D connector and wherein the D connector is on the rack. In some embodiments the rack comprises a plurality of D connectors that can couple to each of the modules of the tissue scaffold through a C connector on each module. In some embodiments the first module and/or the second module and/or the rack further comprise a ridge designed to be melted by the application of energy, wherein the application of energy to the ridge fuses the first module or the second module to the rack, and wherein the ridge is on the C connector and/or on the D connector.

In some embodiments the rack comprises a trough shaped portion having two side regions, a proximal end and distal end. In some embodiments the rack further comprises a bottom region, wherein the modules fit into the trough shaped region by contacting the bottom region and substantially spanning the two side regions. In some embodiments the rack further comprises D connectors in the bottom of the trough shaped region that couple to C connectors on the modules where the modules contact the bottom of the trough shaped region. In some embodiments the D connector is a recess and the C connector is a protuberance on the module, wherein the protuberance fits into the recess. In some embodiments the D connector is a protuberance and the C connector is a recess on the module, wherein the protuberance fits into the recess.

In some embodiments the rack spans a bone gap in a mammal and the modules fill the gap. In some embodiments the bone gap is in a long bone. In some embodiments the rack spans the long bone gap by the ends of the trough shaped region partially enveloping the long bone. In some embodiments the bone is a mandible of a living mammal. In some embodiments the rack spans a gap in the body of a mandible by the ends of the trough shaped region partially enveloping the body of the mandible. In some embodiments the rack comprises a bar which the modules at least partially envelop. In some embodiments the rack is not degradable. In some embodiments the rack is degradable.

In some embodiments the rack has a porous microstructure, the rack is synthesized from polycaprolactone, and the rack is substantially coated with calcium-deficient carbonate-containing hydroxyapatite.

In some embodiments each tissue scaffold module and/or the rack further comprises a ridge designed to be melted by the application of energy, wherein the application of energy to the ridge fuses at least one of the modules to at least another module and/or the rack. In some embodiments the dovetail connectors are elliptical.

In an embodiment of a method of filling a tissue gap, the method comprises inserting the tissue scaffold of an embodiment described above into the tissue gap. In another embodiment the method further comprises fusing the first module to the second module by placing a liquefied biocompatible polymer between the first module and the second module such that the polymer hardens and fuses the first module to the second module. In another embodiment the method further comprises applying energy to the ridge such that the ridge melts and fuses the first module to the second module.

In another embodiment, the method comprises partially enveloping the gap in the long bone with the rack such that the rack spans the gap, inserting a module into the trough shaped region of the rack such that the module spans the two top edges of the trough shaped region, and inserting additional modules into the trough shaped region as necessary to fill the gap, wherein the modules couple with each other at the dovetail connector. In another embodiment the method further comprises fusing the modules to each other and/or to the rack by placing a liquefied biocompatible polymer between each of the modules and/or between the modules and the rack such that the polymer hardens and fuses the first module to the second module and/or the rack.

In another embodiment of the method each tissue scaffold module and/or the rack further comprise a ridge designed to be melted by the application of energy, wherein energy is applied to the ridge such that at least one of the modules is fused to at least another module and/or the rack. In another embodiment of the method the tissue gap is in a mandible of a mammal, and the method comprises partially enveloping the gap in the mandible with the rack such that the rack spans the gap, inserting a module into the trough shaped region of the rack such that the module spans the two top edges of the trough shaped region, and inserting additional modules into the trough shaped region as necessary to fill the gap, wherein the modules couple with each other at the dovetail connector. In another embodiment the method further comprises fusing the modules to each other and/or to the rack by placing a liquefied biocompatible polymer between each of the modules and/or between the modules and the rack such that the polymer hardens and fuses the first module to the second module and/or the rack.

In another embodiment the tissue scaffold further comprises at least one pin, wherein the at least one pin is used to couple the tissue scaffold to tissue.

In another embodiment the tissue is bone. In another embodiment the at least one pin is made from a biodegradable and absorbable material. In another embodiment the at least one pin is coupled to the tissue scaffold and adjacent tissue. In another embodiment the coupling is accomplished by at least one of sonically welding and applying energy to bond the at least one pin to the tissue scaffold and the adjacent tissue. In another embodiment the pin is synthesized from a material independently selected from a degradable polymer and a mixture of a degradable polymer and a bioceramic. In another embodiment the polymer is polycaprolactone, polylactide, polyglycolide, poly(lactide-glycolide), poly(propylene fumarate), poly(caprolactone fumarate), polyethylene glycol, poly(glycolide-co-caprolactone), or mixtures thereof. In another embodiment the polymer is polycaprolactone.

In another embodiment the pin comprises an osteoconductive mineral coating on at least a portion of the pin. In another embodiment the osteoconductive mineral coating is hydroxyapatite, calcium-deficient carbonate-containing hydroxyapatite, tricalcium phosphate, amorphous calcium phosphate, octacalcium phosphate, dicalcium phosphate, calcium phosphate, or a mixture thereof. In another embodiment the osteoconductive mineral coating is calcium-deficient carbonate-containing hydroxyapatite.

In another embodiment the pin comprises a bioactive agent. In another embodiment the bioactive agent is present in an amount that induces ossification. In another embodiment the bioactive agent is a bone morphogenetic protein (BMP), demineralized bone matrix, a bone marrow aspirate, a transforming growth factor, a fibroblast growth factor, an insulin-like growth factor, a platelet derived growth factor, a vascular endothelial growth factor, a growth and development factor-5, platelet rich plasma, or a mixture thereof.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIGS. 1A-B are images showing a sleeve design for a mandibular condyle reconstruction. FIG. 1A shows a longitudinal view of sleeve highlighting internal raised slots for module insertion. FIG. 1B shows a transverse view showing overall sleeve design.

FIG. 5A shows initial creation of a 3.5 cm mandibular segmental defect. FIG. 5B shows initial sizing of scaffold sleeve with pins (rectangular highlight) located in drill holes. FIG. 5C shows final scaffold implantation and welding of modules (upper middle rectangular highlight) and welding of pins (middle flanking rectangular highlights).

FIG. 6A shows a 3D reconstruction of a bone bridging original defect (defect margins shown by vertical lines). FIG. 6B shows bone growing in scaffold module with module pore structure (rectangular highlight). FIG. 6C shows bone file in a second pig defect.

FIG. 7A shows dual pin tracts in mandible (tracts outlined with four solid straight lines). FIG. 7B is an image two slices away (1.2 mm) from FIG. 7A showing bone formation (circular highlight) underneath lower pin tract (tracts outlined with two solid straight lines).

DETAILED DESCRIPTION OF THE INVENTION

Provided herewith are scaffolds 10 with modular components that can be used for tissue reconstruction, e.g., to fill defects of variable sizes. The scaffolds 10 comprise biocompatible or degradable tissue modules 30, a variable number of which can fill a defect of any size.

Figure 3:
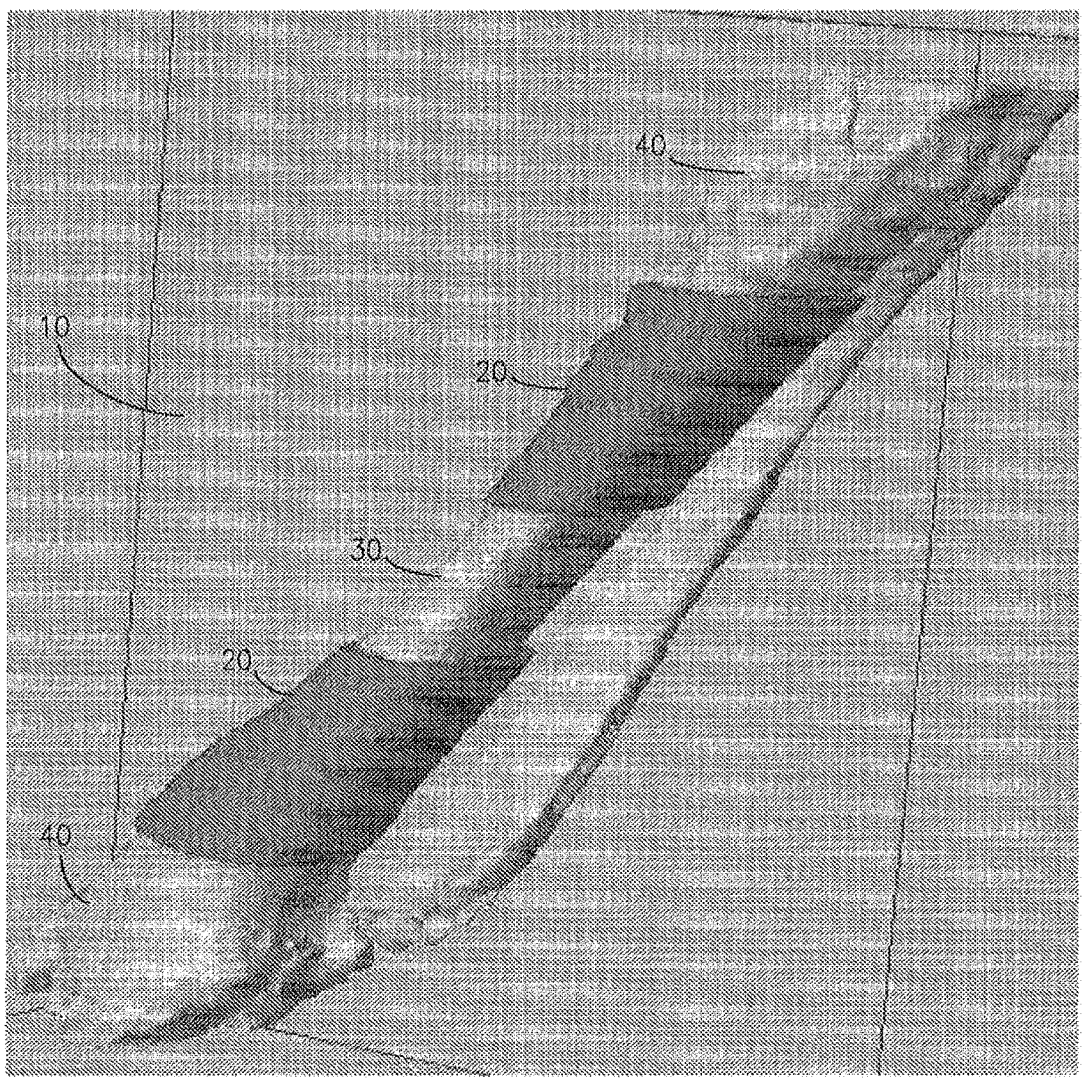
FIG. 3 is an image showing a sleeve module design applied to a tibial segmental defect. The outer ends of the bone are the remaining tibia, the middle section represents the module region, and the pair of wrapped sections between the outer ends and middle represent a sleeve area attached to the remaining bone. Modules can also be contained using a central core.

A scaffold 10 provided herein can be used to fill any type of tissue defect, for example a soft tissue defect, a cartilage defect, or a bone defect 45. A scaffold 10 described herein can be used for long bones or any other anatomic regions. For example, a scaffold 10 having a rack 20, in the form of two sleeves containing a central region, and one or more modules 30 can be used to fill a defect in a long bone (see e.g., FIG. 3). At least one advantage of a modular design is the ability to adjust a dimension (e.g., length) an implant by adding or removing a module. Such adjustment can be accomplished during a surgery or in an operating room, thus eliminating a need for manufacture of multiple implants each of a different fixed size. Such a design also has advantages for cell, gene, protein, and drug delivery using various coatings. These and other features are discussed further below.

A scaffold 10 described herein can have mechanical properties the same or substantially similar to that of bone 40. Thus stress shielding can be avoided. Because various embodiments of the implantable scaffold 10 can be resorbed and replaced by native bone 40, problems associated with wear debris and long term foreign body reactions can be reduced. A scaffold 10 or component can be fabricated from polymer materials described herein. Some polymers provide for a radiolucent implantable scaffold 10. A scaffold 10 or component described herein can include an osteoconductive coating that can bind to one or more optional osteoinductive agents (e.g., a agent naturally occurring in the body of a subject or an agent introduced peri-operatively). A scaffold 10 or component described herein can be osteoinductive or provide for release of factors in a temporally or spatially controlled manor from one or more components or modules 30.

Described herein is an implantable scaffold 10 that can include one or more modular components, a tissue scaffold rack 20, or some combination thereof. The rack 20 can interface with tissue, such as bone 40, near to a tissue defect. For example, the rack 20 can interface with bone 40 surrounding or flanking a bone defect 45. The rack 20 can accommodate one or more scaffold modules 30. For example, one or more modules 30 can be placed in or on a scaffold rack 20 such that the module(s) partially or substantially fill a tissue defect.

A scaffold 10 described herein can be implanted to correct a tissue defect in bone 40 tissue. For example, a scaffold 10 can span a tissue defect, such as a gap. A scaffold 10 can be implanted in a vertebrate subject, such as a mammal subject. For example, a scaffold 10 can span and fill or substantially fill a bone gap in a mammal. As another example, a scaffold 10 can span a bone gap (e.g., a long bone gap) with the ends of the scaffold rack 20 partially or substantially enveloping the bone 40 and one or modules 30 filling or substantially filled the gap. A scaffold 10 can be designed to correct a tissue defect in a bone 40 mandible of a living mammal. For example, a scaffold 10 can span a gap in the body of a mandible with the ends of the scaffold rack 20 partially or substantially enveloping the body of the mandible and one or modules 30 filling or substantially filled the gap in the mandible.

Design of Scaffold

Scaffold 10 design can be according to U.S. Pat. No. 7,174,282, which provides a non-limiting example of a design methodology for creating biomaterial scaffolds 10 with internal porous architectures that meet the need for mechanical stiffness and strength and the need for connected porosity for cell migration and tissue regeneration (see also, US Pat App Pub No. 2008/0195211, US Pat App Pub No. 2008/0215093 and US Pat App Pub No. 2006/0276925). Design methods, such as those described in US Pat App Pub No. 2003/0069718 can combine image-based design of structures with homogenization theory to compute effective physical property dependence on material microstructure. Optimization techniques can then be used to compute the optimal geometry. The final optimized scaffold 10 geometry voxel topology can be combined with a voxel data set describing the three dimensional anatomic scaffold 10 shape which may be obtained by imaging techniques such as magnetic resonance (MR) images or combined MR and computed tomography (CT) images. Density variations within the anatomic scaffold 10 voxel database can be used as a map to guide where different optimized scaffold 10 voxel topologies are substituted. The final voxel representation of the anatomically shaped scaffold 10 with optimized interior architecture can then be converted automatically by software into either a surface representation or wire frame representation for fabrication of the scaffold 10 by way of solid free form fabrication or casting.

The methods described in US Pat App Pub No. 2006/0276925 also provide a design methodology for creating biomaterial scaffolds 10 with internal porous architectures that can provide adequate mechanical stiffness and strength for any scaffold, and the need for connected porosity for cell migration and tissue regeneration. The methods of US Pat App Pub No. 2006/0276925 can be used to generate a scaffold 10 with a designed periodic microstructure that attains desired stability (displacements <0.9 mm), while maintaining compliance to avoid stress shielding and a large porosity for biofactor delivery.

Using any of the methods described herein, once a scaffolding image-design dataset is created, it can be automatically converted into a surface representation in, for example, .stl file format (stereolithography triangular facet data). This makes it possible to fabricate the scaffolding from any type of Solid Free-Form Fabrication (SFF) system using either direct or indirect methods. Direct SFF methods include, but are not limited to: (1) Selective Laser Sintering (SLS); (2) Stereolithography (SLA); (3) Fused Deposition Modeling (FDM); (4) 3D printing (3DP), and (5) Selective Laser Melting (SLM). Conventional design of the scaffolds 10 and newer design by degradation topology optimization can be exported to an EOS Formega P 100 machine (3D Systems, Valencia, Calif., USA) in .stl file format, and can be used to construct scaffolds 10 by SLS processing of e.g., ε-polycaprolactone powder. This particular form of polycaprolactone has a melting point of 60° C., a molecular weight in the range of 35,000 to 100,000 Daltons, and particle size distribution in the 25-100 pm range. However, nanoscale particle sizes can also be suitable in place of the microscale particle sizes. Scaffolds 10 are built layer-by-layer using a powder layer thickness of, e.g., 100 pm. After SLS processing is completed, the scaffold 10 is allowed to cool inside the machine process chamber and is then removed from the part bed. Excess powder surrounding the cages is brushed off and the scaffolds 10 are finally cleaned by blowing compressed air and physically removing unsintered powder from the cage interstices by insertion of a 1 millimeter diameter wire.

In some embodiments, SLS parameters are divided into five main categories—Contour 1, Contour 2, Edge 1, Edge 2, and Hatching.

Modules

Implantable scaffolds 10 described herein can include one or more modules 30. A scaffold 10 can comprise modular inserts 30 with a designed porosity that can be fitted within a rack 20 designed to fit an anatomical region or a center core that runs between two anatomical regions. For example, a scaffold 10 can contain one or more modules 30 that fit in or on a rack 20 that interfaces with a tissue proximate to a defect.

A tissue scaffold module 30 can be made all or in part of a biocompatible material. For example, a module 30 can be a polymer, such as a degradable polymer. A module 30 can be degradable. A module 30 can be degradable when implanted into a subject, such as a mammal. A module 30 can be non-degradable. A module 30 can be formed in whole or in part of a polymer, such as a degradable polymer. Polymer materials suitable for a module 30 can be as discussed herein.

A module 30 can have a porous microstructure in all or part of the module 30. An internal porous microstructure of a module 30 can be created using an image-based design technique, such as that described in U.S. Pat. No. 7,174,282.

Shape

A scaffold module 30 can have a shape designed to mimic or substantially mimic a contour of a non-defective or healthy tissue in the region of a tissue defect. A plurality of modules 30 can in combination mimic or substantially mimic a contour of a non-defective or healthy tissue in the region of a tissue defect fill or substantially fill a tissue defect. For example, a plurality of modules 30 can in combination fill or substantially fill a tissue defect such that the contours of a healthy or non-defective tissue are provided in the region of the defect. A scaffold module 30 can have an external shape created using an image-based design technique. Exemplary image-based design techniques are described in U.S. Pat. No. 7,174,282, incorporated herein by reference.

Figure 2:
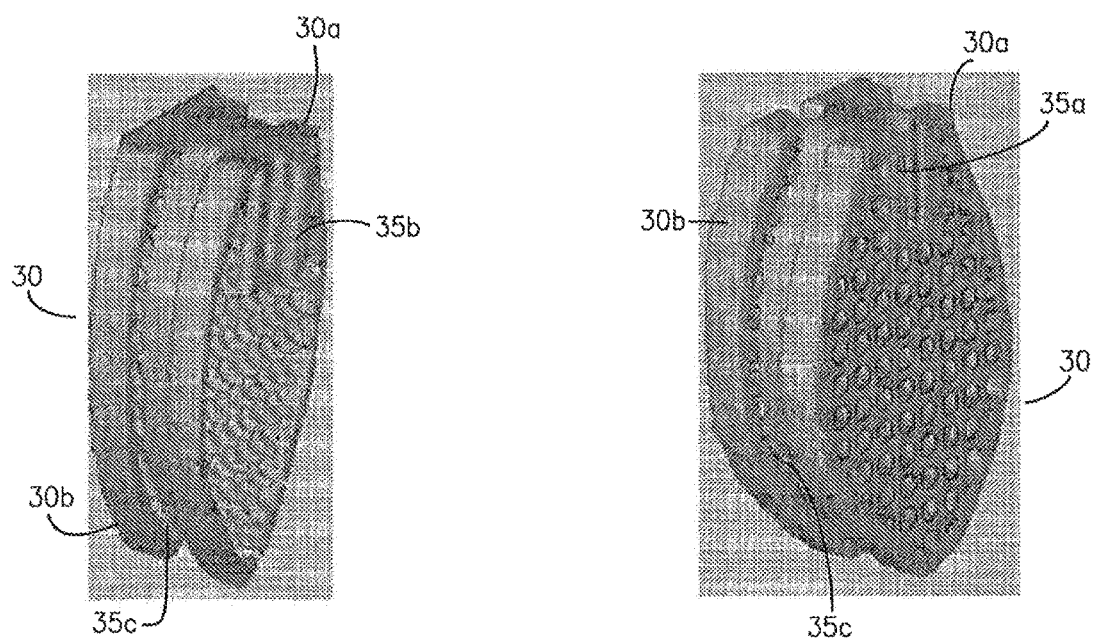
FIG. 2 is an image showing a module design with slots for mating into sleeve fixation and dovetail joint for fitting each module together.

A scaffold module 30 can have an irregular disk shape. A scaffold module 30 having an irregular disk shape can have one or more flat or substantially flat sides. For example, a scaffold module 30 can have an irregular disk shape with two flat sides (see e.g., FIG. 2). A scaffold module 30 can have a circumference substantially in the form of an outline of missing or damaged tissue in, for example, a tissue gap. A plurality of scaffold modules 30 having a circumference substantially in the form of an outline of missing or damaged tissue can combine to fill or substantially fill a tissue defect, such as a gap (see e.g., FIG. 4).

An implantable scaffold 10 described herein can have one or more modules 30. For example, a scaffold 10 can have a first module 30a. As another example, a scaffold 10 can have a second module 30b. As another example, a scaffold 10 can have a third module 30c. As another example, a scaffold 10 can have a fourth module 30d. As another example, a scaffold 10 can have a fifth module 30e. As another example, a scaffold 10 can have a sixth module 30. As another example, a scaffold 10 can have a seventh module 30. As another example, a scaffold 10 can have an eighth module 30. As another example, a scaffold 10 can have a ninth module 30. As another example, a scaffold 10 can have a tenth module 30. As another example, a scaffold 10 can have more than ten module 30.

In a scaffold 10 with a plurality of modules 30, one or modules 30 can be an end module 30a or 30e (e.g., a module proximate to tissue). An end module 30a or 30e can have one or more projection that can interface with proximate tissue. For example, an end module 30a or 30e can have projection that can fit into a marrow space of a surrounding bone 40.

A scaffold 10 design can incorporate any number of modules 30 of any thickness with any necessary or desired geometric shape. Such design does not have to be limited to cylinders of conventional designs. It is understood that a scaffold 10 can have as many modules 30 as necessary or desired to fill or substantially fill a defect. The number of modules 30 of a scaffold 10 can be according to the design of the module 30 (e.g., thickness) and the size of a tissue defect. The number of modules 30 necessary to fill or substantially fill a tissue defect can be determined in advance. The number of modules 30 necessary to fill or substantially fill a tissue defect can be determined during a procedure, such as a surgery to correct a tissue defect.

Connectors

A scaffold module 30 can have one or more connectors 35. A connector 35 of a module 30 can couple the module 30 to another component of the scaffold 10. For example, a module 30 can have a connector 35 that couples that module 30 to another module 30. As another example, a module 30 can have a connector 35 that couples that module 30 to a rack 20.

A module 30 can have multiple connectors 35. For example, a module 30 can have multiple connectors 35 for coupling that component to one or more other modules 30. As another example, a module 30 can have multiple connectors 35 for coupling that module 30 to one other module 30. As another example, a module 30 can have multiple connectors 35 for coupling that module 30 to a rack 20. As another example, a module 30 can have multiple connectors 35 for coupling that module 30 to one or more other modules 30 and a rack 20.

A connector 35 can permanently or removably couple a module 30 to another component of a scaffold 10.

A connector 35 of a module 30 can have a shape suitable for connecting to another component of a scaffold 10. For example, a connector 35 can be shaped for snap fit, mortise and tenon, dovetail or other joints. A module 30 can include one or more connectors 35 having the same shape or different shapes. Shape of a module connector 35 can complement the shape of a connector 25 or 35 of a scaffold 10 component to be coupled.

A scaffold module 30 can include a connector(s) 35 in the form of a slot(s), e.g., a raised slot. A raised slot connector 35 of a module 30 can mate with a slot in or on another module 30 or a rack 20. Methods of fixing a module 30 to a rack 20 include, but are not limited to, snap fit, mortise and tenon, dovetail or similar joints. In addition to fitting within the fixation sleeve, one or more scaffold modules 30 can have associated snap fit, mortise and tenon, dovetail or similar joint to lock together. A connector 35 can be a dovetail connector 35. A connector 35 can be an elliptical dovetail connector 35.

A connector 35 can be or include a ridge that functions to connect a module 30 to another module 30 or to a rack 20 or both. A connector 35 can include a ridge designed to be melted by, for example, the application of energy, such as, for example, heat or ultrasound. Application of energy to the ridge can fuse the a module 30 to another module 30, to a rack 20, or both.

A connector 35 can be a liquefied biocompatible polymer. A liquefied biocompatible polymer connector 35 can harden or fuse one module 30 to another module 30 or to a rack 20 or both.

A first module 30a can have an A connector 35a. The A connector 35a of a first module 30a can connect to a B connector 35b of a second module 30b. An A connector 35a of a first module 30a and a B connector 35b of a second module 30b can be the same type of connector 35. An A connector 35a of a first module 30a and a B connector 35b of a second module 30b can be different types of connector 35.

A scaffold module 30 can have a C connector 35c. The C connector 35c of a module 30 can connect to a D connector 25 of a scaffold rack 20. The C connector 35c of a module 30, for connecting a scaffold rack 20, can be included in or on a module 30 along with other connectors 35, e.g., for connecting to other modules 30.

A scaffold module 30 can include a bioactive agent, as described further herein. A scaffold module 30 can include a surface modification or a coating, as described further herein. A scaffold module 30 can include one or more cell types, as described further herein.

Scaffold Rack

Implantable scaffolds 10 described herein can include a tissue scaffold rack 20. A scaffold 10 can comprise a rack 20 designed to accommodate one or more modules 30. The scaffold rack 20 can fit an anatomical region or a center core that runs between two anatomical regions. For example, a scaffold 10 can contain a rack 20 that fits one or more modules 30 that interfaces with a tissue proximate to a defect. For example, a rack 20 can accommodate a first module 30a and a second module 30b (or additional modules 30), which combine to fill or substantially fill a tissue defect.

A tissue scaffold rack 20 can be made all or in part of a biocompatible material. For example, a rack 20 can be a polymer, such as a degradable polymer. The scaffold rack 20 can comprise a biocompatible material as described herein. The scaffold rack 20 can be degradable. The scaffold rack 20 can be degradable when implanted into a subject, such as a mammal. The scaffold rack 20 can be non-degradable. The scaffold rack 20 can be formed in whole or in part of a polymer, such as a degradable polymer. Polymer materials suitable for the scaffold rack 20 can be as discussed herein.

A rack 20 can have a porous microstructure in all or part of the rack 20. An internal porous microstructure of a rack 20 can be created using an image-based design technique, such as that described in U.S. Pat. No. 7,174,282.

An implantable scaffold 10 described herein can have a rack 20 that accommodates one or more modules 30. For example, a rack 20 can accommodate at least one, at least two, at least three, at least four, at least five, at least six, at least seven, at least eight, at least nine, at least ten, or more modules 30.

Shape

A scaffold rack 20 can have a shape designed to mimic or substantially mimic a contour of a non-defective or healthy tissue in the region of a tissue defect. A rack 20 can accommodate a plurality of modules 30 that in combination mimic or substantially mimic a contour of a non-defective or healthy tissue in the region of a tissue defect fill or substantially fill a tissue defect. For example, a rack 20 that accommodates a plurality of modules 30 can in combination fill or substantially fill a tissue defect such that the contours of a healthy or non-defective tissue are provided in the region of the defect. A scaffold rack 20 can have an external shape created using an image-based design technique. Exemplary image-based design techniques are described in U.S. Pat. No. 7,174,282, incorporated herein by reference.

The shape of a scaffold rack 20 can be designed to span a tissue defect, such as a gap. A scaffold rack 20 can span a tissue gap in a vertebrate. The shape of a scaffold rack 20 can be designed to conform or substantially conform to the contours of a healthy or non-defective tissue so as to span a tissue defect, such as a gap. For example, a scaffold rack 20 can span a bone gap. As another example, a scaffold rack 20 can span a long bone gap. As another example, a scaffold rack 20 can span a bone gap in a mammal and one or more scaffold modules 30 fill the gap.

A scaffold rack 20 can comprise a bar, which the modules 30 at least partially envelop.

A scaffold rack 20 can have a trough shaped portion. A trough shaped portion of a scaffold rack 20 can have multiple (e.g., two) side regions 21, a proximal end 24 and a distal end 26. A rack 20 can span a bone gap (e.g., a long bone gap) by the proximal end 24 or distal end 26 of the trough shaped region partially or substantially enveloping the bone 40. A trough shaped portion of a scaffold rack 20 can have a bottom region 22 that accommodates one or more modules 30 into the trough shaped region by contacting the bottom region 22 and substantially spanning the two side regions 21.

A scaffold rack 20 can span a tissue defect, such as a gap or bone gap, in a subject, such as a vertebrate or mammalian subject. For example, a scaffold rack 20 can span a bone gap (e.g., a long bone gap) with the proximal end 24 or distal end 26 of the rack 20 partially or substantially enveloping the bone 40. The rack 20 thus interfaced with the bone can accommodate one or modules 30 that fill or substantial fill the gap. For example, a scaffold rack 20 can span a gap in the body of a mandible with the proximal end 24 or distal end 26 of the rack partially or substantially enveloping the body of the mandible, where the rack 20 accommodates one or modules 30 filling or substantially filled the gap in the mandible.

Connectors

A scaffold rack 20 can have one or more connectors 25 for connecting the rack 20 to other components of the scaffold 10 or to tissue.

A scaffold rack 20 can have one or more connectors 25. A connector 25 of a rack 20 can couple one or more modules 30 to the rack 20. One or modules 30 can be joined to the scaffold rack 20 as described further herein. A connector 25 of a rack 20 can couple that rack 20 to another scaffold rack 20.

A connector 25 can permanently or removably couple a rack 20 to another component of a scaffold 10.

A connector 25 of a rack 20 can have a shape suitable for connecting to another component of a scaffold 10. For example, a connector 25 can be shaped for snap fit, mortise and tenon, dovetail or other joints. A rack 20 can include one or more connectors 25 having the same shape or different shapes. Shape of a rack connector 25 can complement the shape of a connector 25 or 35 of another scaffold 10 component, such as a module 30.

A scaffold rack 20 can include a connector(s) 25 in the form of a slot(s) (see e.g., FIG. 1A), e.g., a raised slot. A raised slot connector 25 of a rack 20 can mate with a slots in or on one or more scaffold modules 30. Methods of fixing a rack 20 to a module 30 include, but are not limited to, snap fit, mortise and tenon, dovetail or similar joints. In addition to fitting within a rack 20, one or more scaffold modules 30 can have associated snap fit, mortise and tenon, dovetail or similar joint to lock together. A rack connector 25 can be a dovetail connector 25. A rack connector 25 can be a an elliptical dovetail connector 25.

A connector 25 can be or include a ridge that functions to connect a rack 20 to another component of the scaffold, such as a module 30. A connector 25 can include a ridge designed to be melted by, for example, the application of energy. Application of energy to the ridge can fuse the rack 20 to another component of the scaffold, such as one or more modules 30 or different rack 20, or both.

A connector 25 can be a liquefied biocompatible polymer. A liquefied biocompatible polymer connector 25 can harden or fuse a rack 20 to another component of the scaffold, such as one or more modules 30.

A scaffold rack 20 can have a D connector 25. The D connector 25 of a rack 20 can connect to a C connector 30c of a module 30. The D connector 25 of a rack 20, for connecting a module 30, can be included in or on a rack 20 along with other connectors 25. A plurality of D connectors 25 on a rack 20 can couple to one or modules 30 in or on the rack 20 through, for example, a C connector 30c of a module 30. One or more D connectors 25 can be in the bottom 22 of a trough shaped region of the rack 20 that couple to C connectors 30c on the modules 30, where the modules 30 contact the bottom 22 of the trough shaped region.

A D connector 25 can be in a recess of the rack 20 and a C connector 30c can be in a protuberance of a module 30, wherein the protuberance fits into the recess. A D connector 25 can be on a protuberance of the rack 20 and a C connector 30c can be in a recess of a module 30, wherein the protuberance fits into the recess.

A scaffold rack 20 can include a bioactive agent, as described further herein. A scaffold rack 20 can include a surface modification or a coating, as described further herein. A scaffold rack 20 can include one or more cell types, as described further herein.

Scaffold Materials

A scaffold 10 described herein can include one or more components fabricated in whole or in part from a polymer material, such as a degradable polymer material, a porous polymer material, or a degradable porous polymer material. Suitable scaffold materials are discussed in, for example, Ma and Elisseeff, ed. (2005) Scaffolding in Tissue Engineering, CRC, ISBN 1574445219; Saltzman (2004) Tissue Engineering: Engineering Principles for the Design of Replacement Organs and Tissues, Oxford ISBN 019514130X.

A scaffold 10 made in whole or in part from a polymer material can: provide structural and/or functional features of the target tissue (e.g., bone 40); allow cell attachment and migration; deliver and retain cells and biochemical factors; enable diffusion of cell nutrients and expressed products; or exert certain mechanical and biological influences to modify the behavior of the cell phase. Scaffold materials can be biocompatible materials that generally form a porous, microcellular matrix, which can provide a physical support or an adhesive substrate for introducing bioactive agents or cells during fabrication, culturing, or in vivo implantation.

Generally, a biocompatible material is one which stimulates at most only a mild, often transient, implantation response, as opposed to a severe or escalating response. A biodegradable or degradable material is generally understood to decomposes under normal in vivo physiological conditions into components which can be metabolized or excreted.

Material biodegradability can provide for absorption of the matrix by the surrounding tissues and can eliminate the necessity of a surgical removal. The rate at which degradation occurs can coincide as much as possible with the rate of tissue formation. Thus, while cells are fabricating their own natural structure around themselves (see e.g., FIG. 6B), the scaffold 10 or components thereof can provide structural integrity and eventually break down leaving the neotissue, newly formed tissue which can assume the mechanical load. One or more scaffold materials can be modified so as to increase biodegradability. For example, PCL is a biodegradable polyester by hydrolysis of its ester linkages in physiological conditions, and can be further modified with ring opening polymerization to increase its biodegradability.

Nonlimiting examples of suitable biodegradable materials include polycaprolactone, polylactide, polyglycolide, poly (lactide-glycolide), poly(propylene fumarate), poly(caprolactone fumarate), polyethylene glycol, and poly(glycolide-co-caprolactone), polysaccharides (e.g. alginate), chitosan, polyphosphazene, polyacrylate, polyethylene oxide-polypropylene glycol block copolymer, fibrin, collagen, fibronectin, polyvinylpyrrolidone, hyaluronic acid, polycarbonates, polyamides, polyanhydrides, polyamino acids, polyortho esters, polyacetals, polycyanoacrylates, polyurethanes, polyacrylates, ethylene-vinyl acetate polymers and other acyl substituted cellulose acetates and derivatives thereof, and analogs, mixtures, combinations and derivatives of any of the above In some embodiments, a scaffold, or portion or component thereof, comprises a material having a porous microstructure. Pores of a scaffold, or portion or component thereof, can mimic internal bone 40 structure, allow adherence of cells, provide an open volume for seeding of cells, provide an open volume for growth factors or other additives, allow adherence of another matrix layer, serve as conduits for vascularization, provide internal bone 40 features, or facilitate perfusion. A scaffold material with a high porosity and an adequate pore size is preferred so as to facilitate cell introduction and diffusion throughout the whole structure of both cells and nutrients. Pores of a scaffold material can be engineered to be of various diameters. For example, the pores of a scaffold material can have a diameter range from micrometers to millimeters. As another example, the pores of the matrix material have a diameter of about 100 µm to about 600 µm (e.g., about 150 µm, about 200 µm, about 250 µm, about 300 µm, about 350 µm, about 400 µm, about 450 µm, about 500 µm, or about 550 µm). It is understood that the pores of a scaffold material can have the same, approximately the same, or different average diameters between different components or portions of a scaffold 10. For example, a first module 30a can have a first average pore diameter, a second module 30b can have a second average pore diameter, and the first average pore diameter can be the same, approximately the same, or different than the second average pore diameter. As another example, scaffold modules 30 can have a first average pore diameter, a scaffold rack 20 can have a second average pore diameter, and the first average pore diameter can be the same, approximately the same, or different than the second average pore diameter.

A scaffold, or portion or component thereof, can be produced from proteins (e.g. extracellular matrix proteins such as fibrin, collagen, and fibronectin), polymers (e.g., polyvinylpyrrolidone), polysaccharides (e.g. alginate), hyaluronic acid, or analogs, mixtures, combinations, and derivatives of the above.

A scaffold, or portion or component thereof, can be formed of synthetic polymers. Such synthetic polymers include, but are not limited to, poly(ethylene) glycol, bioerodible polymers (e.g., poly(lactide), poly(glycolic acid), poly(lactide-co-glycolide), poly(caprolactone), polyester (e.g., poly-(L-lactic acid), polyanhydride, polyglactin, polyglycolic acid), polycarbonates, polyamides, polyanhydrides, polyamino acids, polyortho esters, polyacetals, polycyanoacrylates), polyphosphazene, degradable polyurethanes, non-erodible polymers (e.g., polyacrylates, ethylene-vinyl acetate polymers and other acyl substituted cellulose acetates and derivatives thereof), non-erodible polyurethanes, polystyrenes, polyvinyl chloride, polyvinyl fluoride, polyvinyl pyrrolidone, poly(vinylimidazole), chlorosulphonated polyolifins, polyethylene oxide, polyvinyl alcohol (e.g., polyvinyl alcohol sponge), synthetic marine adhesive proteins, Teflon®, nylon, or analogs, mixtures, combinations (e.g., polyethylene oxide-polypropylene glycol block copolymer; poly(D,L-lactide-co-glycolide) fiber matrix), and derivatives of the above.

A scaffold, or portion or component thereof, can be formed of naturally occurring polymers or natively derived polymers. Such polymers include, but are not limited to, agarose, alginate (e.g., calcium alginate gel), fibrin, fibrinogen, fibronectin, collagen (e.g., a collagen gel), gelatin, hyaluronic acid, chitin, and other suitable polymers and biopolymers, or analogs, mixtures, combinations, and derivatives of the above. Also, a scaffold, or portion or component thereof, can be formed from a mixture of naturally occurring biopolymers and synthetic polymers.

A scaffold, or portion or component thereof, can comprise a crystalline or mineral component. For example, A scaffold, or portion or component thereof, can include the inorganic mineral hydroxyapatite (also known as hydroxylapatite). About seventy percent of natural bone is made up of hydroxyapatite. In some embodiments, a scaffold, or portion or component thereof, comprises a ground natural substance containing hydroxyapatite, such as bone. In some embodiments, a scaffold, or portion or component thereof, comprises substantially pure hydroxyapatite.

A scaffold, or portion or component thereof, can comprise a composite material comprising at least two components described above. As an example, a composite scaffold material can comprise at least three, at least four, at least five, at least six, at least seven, at least eight, at least nine, at least ten, or more, components. The plurality of components can be homogenously mixed throughout the scaffold, heterologously mixed throughout the scaffold, or separated into different layers of the scaffold, or a combination thereof.

In some embodiments, a scaffold, or portion or component thereof, comprises polycaprolactone, polylactide, polyglycolide, poly(lactide-glycolide), poly(propylene fumarate), poly(caprolactone fumarate), polyethylene glycol, poly(glycolide-co-caprolactone), or mixtures thereof.

For example, a scaffold, or portion or component thereof, can be formed in whole or in part of polycaprolactone or a mixture, composite, or derivative thereof. Polycaprolactone can be a particularly useful material where the scaffolds 10 are prepared by the methods described in U.S. Pat Pub No. 2003/0069718, U.S. Pat Pub No. 2006/0276925, U.S. Pat Pub No. 2008/0195211, U.S. Pat Pub No. 2008/0215093, or U.S. patent application Ser. No. 13/036,470, all are incorporated herein by reference in their entireties.

Surface Coating

A scaffold, or portion or component thereof, described herein can include a surface modification or a coating. A modular scaffold 10 design can allow for homogenous or heterogenous surface modification techniques or drug delivery.

Where a scaffold 10 is designed to fill a bone defect 45, an osteoconductive mineral coating can be utilized. An osteoconductive mineral coating can comprises a plurality of discrete mineral islands on the scaffold, or the mineral coating can be formed on the entire surface of the scaffold 10. In one exemplary form, the osteoconductive mineral coating comprises a substantially homogeneous mineral coating. In other embodiments, the mineral coatings may be any suitable coating material containing calcium and phosphate, such as hydroxyapatite, calcium-deficient carbonate-containing hydroxyapatite, tricalcium phosphate, amorphous calcium phosphate, octacalcium phosphate, dicalcium phosphate, calcium phosphate, and the like. The mineral coating may also include a plurality of layers having distinct dissolution profiles to control dissolution order, kinetics and bioactive delivery properties.

To induce formation of a calcium phosphate-based mineral layer, the scaffold 10 in some embodiments is incubated in modified simulated body fluid (mSBF) solutions for mineral nucleation and growth. The mSBF solution can contain ionic constituents of blood plasma, with double the concentrations of calcium and phosphate ions, held at physiologic temperature and pH 6.8. The growth of calcium phosphate-based minerals, specifically bone-like minerals, on bioresorbable polymer matrices using mSBF incubation has been demonstrated (Lin et al., 2004; Murphy et al., 2002, 2005).

A scaffold, or portion or component thereof, can be coated individually or in groups using, for example, a CaP coating technology. A scaffold, or portion or component thereof, can be modified individually or in groups using a technique such as aminolysis for RGD attachment, chemical conjugation, layer by layer deposition, or chemical vapor deposition.

A scaffold, or portion or component thereof, can have the same or similar surface modification or coating as another component. A scaffold, or portion or component thereof, can have a different surface modification or coating as other components. A module 30 can have the same or different surface modification or coating as other modules 30 of the scaffold 10. Thus is provided spatial control over release of growth factors or drugs.

A scaffold, or portion or component thereof, can comprise an osteoconductive mineral coating. For example, one or more modules 30 of a scaffold 10 can be coated with a composition comprising a scaffold, or portion or component thereof, can comprise an osteoconductive. An osteoconductive mineral coating can include one or more of is hydroxyapatite, calcium-deficient carbonate-containing hydroxyapatite, tricalcium phosphate, amorphous calcium phosphate, octacalcium phosphate, dicalcium phosphate, calcium phosphate, or a mixture thereof. For example, an osteoconductive mineral coating can be calcium-deficient carbonate-containing hydroxyapatite.

Cells

In various embodiments of scaffolds 10 described herein, cells can be introduced (e.g., implanted, injected, infused, or seeded) into or onto a scaffold, or portion or component thereof. Cells can be derived from the intended recipient of the scaffold, or from another donor. Additionally, the cell can be a primary cell, i.e., taken from the donor without culture, or the cell could be cultured any length of time prior to seeding. Further, the cage can be seeded with cells then incubated under appropriate conditions to allow colonization of the cage to any degree prior to implant.

Different types of cells can be co-introduced or sequentially introduced. Where differing types of cells are employed, they can be introduced in the same spatial position, similar spatial positions, or different spatial positions, relative to each other.

Cells can be introduced into the scaffold, or portion or component thereof, by a variety of means known to the art. Methods for the introduction (e.g., infusion, seeding, injection, etc.) of cells into or into the scaffold material are discussed in, for example, Ma and Elisseeff, ed. (2005) Scaffolding In Tissue Engineering, CRC, ISBN 1574445219; Saltzman (2004) Tissue Engineering: Engineering Principles for the Design of Replacement Organs and Tissues, Oxford ISBN 019514130X; Minuth et al. (2005) Tissue Engineering: From Cell Biology to Artificial Organs, John Wiley & Sons, ISBN 3527311866. For example, cells can be introduced into or onto the matrix by methods including hydrating freeze-dried scaffolds 10 with a cell suspension (e.g., at a concentration of 100 cells/ml to several million cells/ml). Methods of addition of additional agents vary, as discussed below.

Cells can be introduced into or onto a scaffold material at the time of fabrication. For example, cells can be introduced into the scaffold 10 by a bioplotter, or other similar device, during or near the time when biocompatible polymer layers are formed into a 3-dimensional scaffold 10 (e.g., cell printing).

Cells can be introduced into or onto individual modules 30 prior to assembly or joining of the modules 30 to one another or a scaffold rack 20.

Methods of culturing and differentiating cells in or on scaffolds 10 are generally known in the art (see e.g., Saltzman (2004) Tissue Engineering: Engineering Principles for the Design of Replacement Organs and Tissues, Oxford ISBN 019514130X; Vunjak-Novakovic and Freshney, eds. (2006) Culture of Cells for Tissue Engineering, Wiley-Liss, ISBN 0471629359; Minuth et al. (2005) Tissue Engineering: From Cell Biology to Artificial Organs, John Wiley & Sons, ISBN 3527311866). As will be appreciated by one skilled in the art, the time between cell introduction into or onto the scaffold 10 and engrafting the resulting scaffold 10 can vary according to particular application. Incubation (and subsequent replication and/or differentiation) of the engineered composition cells in or on the scaffold material can be, for example, at least in part in vitro, substantially in vitro, at least in part in vivo, or substantially in vivo. Determination of optimal culture time is within the skill of the art. A suitable medium can be used for in vitro progenitor cell infusion, differentiation, or cell transdifferentiation (see e.g., Vunjak-Novakovic and Freshney, eds. (2006) Culture of Cells for Tissue Engineering, Wiley-Liss, ISBN 0471629359; Minuth et al. (2005) Tissue Engineering: From Cell Biology to Artificial Organs, John Wiley & Sons, ISBN 3527311866). The culture time can vary from about an hour, several hours, a day, several days, a week, or several weeks. The quantity and type of cells present in the matrix can be characterized by, for example, morphology by ELISA, by protein assays, by genetic assays, by mechanical analysis, by RT-PCR, and/or by immunostaining to screen for cell-type-specific markers (see e.g., Minuth et al. (2005) Tissue Engineering: From Cell Biology to Artificial Organs, John Wiley & Sons, ISBN 3527311866).

For small scaffolds 10 (<100 cubic millimeters in size), in vitro medium can be changed manually, and additional agents added periodically (e.g., every 3-4 days). For larger scaffolds 10, the culture can be maintained, for example, in a bioreactor system, which may use a minipump for medium change. The minipump can be housed in an incubator, with fresh medium pumped to the matrix material of the scaffold 10. The medium circulated back to, and through, the matrix can have about 1% to about 100% fresh medium. The pump rate can be adjusted for optimal distribution of medium and/or additional agents included in the medium. The medium delivery system can be tailored to the type of tissue or organ being manufactured. All culturing can be performed under sterile conditions.

The present teachings include methods for optimizing the density of cells so as to maximize the regenerative outcome of an implanted scaffold 10. Cell densities in a scaffold 10 can be monitored over time and at end-points. Tissue properties can be determined, for example, using standard techniques known to skilled artisans, such as histology, structural analysis, immunohistochemistry, biochemical analysis, and mechanical properties. As will be recognized by one skilled in the art, the cell densities of cells can vary according to, for example, cell type, tissue or organ type, scaffold material, scaffold volume, infusion method, seeding pattern, culture medium, growth factors, incubation time, incubation conditions, and the like. Generally, cell density in a scaffold, or portion or component thereof, can be, independently, from 0.0001 million cells (M) $ml^{-1}$ to about 1000 M $ml^{-1}$. For example, cells can be present in the scaffold, or portion or component thereof, at a density of about 0.001 M $ml^{-1}$, 0.01 M $ml^{-1}$, 0.1 M $ml^{-1}$, 1 M $ml^{-1}$, 5 M $ml^{-1}$, 10 M $ml^{-1}$, 15 M $ml^{-1}$, 20 M $ml^{-1}$, 25 M $ml^{-1}$, 30 M $ml^{-1}$, 35 M $ml^{-1}$, 40 M $ml^{-1}$, 45 M $ml^{-1}$, 50 M $ml^{-1}$, 55 M $ml^{-1}$, 60 M $ml^{-1}$, 65 M $ml^{-1}$, 70 M $ml^{-1}$, 75 M $ml^{-1}$, 80 M $ml^{-1}$, 85 M $ml^{-1}$, 90 M $ml^{-1}$, 95 M $ml^{-1}$, 100 M $ml^{-1}$, 200 M $ml^{-1}$, 300 M $ml^{-1}$, 400 M $ml^{-1}$, 500 M $ml^{-1}$, 600 M $ml^{-1}$, 700 M $ml^{-1}$, 800 M $ml^{-1}$, or 900 M $ml^{-1}$. It is contemplated that cells can be present in the scaffold, or portion or component thereof, in a range from one density value recited above to another density value recited above.

A cell included in or on a scaffold, or portion or component thereof, can be a vertebrate cell. A cell included in or on a scaffold, or portion or component thereof, can be a mammalian cell. A cell included in or on a scaffold, or portion or component thereof, can be a stem cell. A cell included in or on a scaffold, or portion or component thereof, can be an embryonic stem cell. A cell included in or on a scaffold, or portion or component thereof, can be an adult stem cell. A cell included in or on a scaffold, or portion or component thereof, can be a mesenchymal stem cell. A cell included in or on a scaffold, or portion or component thereof, can be an induced pluripotent stem cell.

In some embodiments, the cell is a terminally differentiated cell, e.g., an osteoblast, a chondrocyte, an adipose cell, a pancreatic beta cell, a muscle cell (skeletal, smooth or cardiac), a hepatocyte, or a kidney cell. In other embodiments, the cell is less differentiated, for example a stem cell such as an embryonic stem cell or an adult stem cell, e.g., a mesenchymal stem cell, a hematopoietic stem cell, or an endothelial stem cell. In various embodiments, the stem cell is derived from a cell isolated in the undifferentiated state. In alternative embodiments, the stem cell is induced (known as induced pluripotent stem cells or iPS cells) from a differentiated cell, by any means known in the art (e.g., by transfection with a transgene or by treatment with a cytokine).

Bioactive Agents

In some embodiments, methods and compositions described herein can further comprise additional agents introduced into or onto the scaffold, or portion or component thereof.

In some embodiments, the scaffold 10 comprises a bioactive agent. A bioactive agent as used herein includes, without limitation, physiologically or pharmacologically active substances that act locally or systemically in the body. A bioactive agent can be a substance used for the treatment, prevention, diagnosis, cure or mitigation of disease or illness, or a substance which affects the structure or function of the body or which becomes biologically active or more active after it has been placed in a predetermined physiological environment. Bioactive agents include, without limitation, enzymes, organic catalysts, nucleic acids including ribozymes and antisense RNA or DNA, organometallics, proteins, demineralized bone matrix, bone marrow aspirate, glycoproteins, peptides, polyamino acids, antibodies, nucleic acids, steroidal molecules, antibiotics, antimycotics, cytokines, fibrin, collagen, fibronectin, vitronectin, hyaluronic acid, growth factors, carbohydrates, statins, oleophobics, lipids, extracellular matrix and/or its individual components, pharmaceuticals, and therapeutics.

Various agents that can be introduced include, but are not limited to, bioactive molecules, biologic drugs, diagnostic agents, and strengthening agents.

A scaffold, or portion or component thereof, can have the same or similar bioactive agent(s) as another component. A scaffold, or portion or component thereof, can have a different bioactive agent(s) as other components. A module 30 can have the same or different bioactive agent(s) as other modules 30 of the scaffold 10.

The scaffold, or portion or component thereof, can comprise at least one bioactive agent. In some embodiments, cells of the scaffold 10 can be, for example, genetically engineered to express the bioactive agent or the bioactive agent can be added to the scaffold 10. The scaffold, or portion or component thereof, can also be cultured in the presence of the bioactive agent. A bioactive agent can be added prior to, during, or after cells (when present) are introduced to the scaffold, or portion or component thereof. A bioactive agent can be present in an amount that induces ossification.

The scaffold, or portion or component thereof, can include a bioactive agent that induces ossification. For example, a scaffold, or portion or component thereof, can include a growth factor (e.g., a growth factor that can induce ossification). As another example, a scaffold, or portion or component thereof, can include an osteoinductive cytokine.

A bioactive agent of the scaffold, or portion or component thereof, can be bone morphogenetic protein (BMP), demineralized bone matrix, bone marrow aspirate, transforming growth factor, fibroblast growth factor, an insulin-like growth factor, platelet derived growth factor, vascular endothelial growth factor, growth and development factor-5, platelet rich plasma, or a mixture thereof.

For example, bioactive agent of the scaffold, or portion or component thereof, can be BMP2 or BMP7.

Non-limiting examples of bioactive molecules include activin A, adrenomedullin, aFGF, ALK1, ALK5, ANF, angiogenin, angiopoietin-1, angiopoietin-2, angiopoietin-3, angiopoietin-4, angiostatin, angiotropin, angiotensin-2, AtT20-ECGF, betacellulin, bFGF, B61, bFGF inducing activity, cadherins, CAM-RF, cGMP analogs, ChDI, CLAF, claudins, collagen, collagen receptors $\alpha_1\beta_1$ and $\alpha_2\beta_1$, connexins, Cox-2, ECDGF (endothelial cell-derived growth factor), ECG, ECI, EDM, EGF, EMAP, endoglin, endothelins, endostatin, endothelial cell growth inhibitor, endothelial cell-viability maintaining factor, endothelial differentiation shpingolipid G-protein coupled receptor-1 (EDG1), ephrins, Epo, HGF, TNF-alpha, TGF-beta, PD-ECGF, PDGF, IGF, IL8, growth hormone, fibrin fragment E, FGF-5, fibronectin, fibronectin receptor $\alpha_5\beta_1$, Factor X, HB-EGF, HBNF, HGF, HUAF, heart derived inhibitor of vascular cell proliferation, IFN-gamma, IL1, IGF-2 IFN-gamma, integrin receptors (e.g., various combinations of a subunits (e.g., $\alpha_1$, $\alpha_2$, $\alpha_3$, $\alpha_4$, $\alpha_5$, $\alpha_6$, $\alpha_7$, $\alpha_8$, $\alpha_9$, $\alpha_E$, $\alpha_V$, $\alpha_{IIb}$, $\alpha_L$, $\alpha_M$, $\alpha_X$) and β subunits (e.g., $\beta_1$, $\beta_2$, $\beta_3$, $\beta_4$, $\beta_5$, $\beta_6$, $\beta_7$, and $\beta_8$)), K-FGF, LIF, leiomyoma-derived growth factor, MCP-1, macrophage-derived growth factor, monocyte-derived growth factor, MD-ECI, MECIF, MMP 2, MMP3, MMP9, urokiase plasminogen activator, neuropilin (NRP1, NRP2), neurothelin, nitric oxide donors, nitric oxide synthases (NOSs), notch, occludins, zona occludins, oncostatin M, PDGF, PDGF-B, PDGF receptors, PDGFR-β, PD-ECGF, PA1-2, PD-ECGF, PF4, P1GF, PKR1, PKR2, PPAR-gamma, PPARy ligands, phosphodiesterase, prolactin, prostacyclin, protein S, smooth muscle cell-derived growth factor, smooth muscle cell-derived migration factor, sphingosine-1-phosphate-1 (S1P1), Syk, SLP76, tachykinins, TGF-β, Tie 1, Tie2, TGF-β receptors, TIMPs, TNF-alpha, TNF-beta, transferrin, thrombospondin, urokinase, VEGF-A, VEGF-B, VEGF-C, VEGF-D, VEGF-E, VEGF, $VEGF_{164}$, VEGI, EG-VEGF, VEGF receptors, PF4, 16 kDa fragment of prolactin, prostaglandins E1 and E2, steroids, heparin, 1-butyryl glycerol (monobutyrin), and nicotinic amide. In other preferred embodiments, the matrix includes a chemotherapeutic agent or immunomodulatory molecule. Such agents and molecules are known to the skilled artisan.

In some embodiments, the bioactive agent is a growth factor such as growth hormone (GH); parathyroid hormone (PTH, including PTH1-34); bone morphogenetic proteins (BMPs), such as BMP2A, BMP2B, BMP3, BMP4, BMP5, BMP6, BMP7 and BMP8; transforming growth factor-α (TGF-α), $TGF-\beta_1$ and $TGF-\beta_2$; fibroblast growth factor (FGF), granulocyte/macrophage colony stimulating factor (GMCSF), epidermal growth factor (EGF), platelet derived growth factor (PDGF), growth and development factor-5 (GDF-5), an insulin-like growth factor (IGF), leukemia inhibitory factor (LIF), vascular endothelial growth factor (VEGF), basic fibroblast growth factor (bFGF), platelet derived growth factor (PDGF), angiogenin, angiopoietin-1, del-1, follistatin, granulocyte colony-stimulating factor (G-CSF), hepatocyte growth factor/scatter factor (HGF/SF), interleukin-8 (IL-8), leptin, midkine, placental growth factor, platelet-derived endothelial cell growth factor (PD-ECGF), platelet-derived growth factor-BB (PDGF-BB), pleiotrophin (PTN), progranulin, proliferin, tumor necrosis factor-a (TNF-a), vascular endothelial growth factor (VEGF), a matrix metalloproteinase (MMP), angiopoietin 1 (ang1), ang2, or delta-like ligand 4 (DLL4).

In some embodiments, particularly where the scaffold 10 is to fill a bone defect 45, the bioactive agent is a BMP such as BMP2, BMP4, BMP7, or BMP14, an IGF, an FGF, a PDGF, GDF-5, a TGF, a VEGF or platelet rich plasma (PRP).

Drugs that can be added to the compositions of the application include immunomodulators and other biological response modifiers. A biological response modifier can encompass a biomolecule (e.g., peptide, peptide fragment, polysaccharide, lipid, antibody) that is involved in modifying a biological response, such as the immune response or tissue growth and repair, in a manner which enhances a particular desired therapeutic effect, for example, the cytolysis of bacterial cells or the growth of tissue-specific cells or vascularization. Drugs can also be incorporated directly into the matrix component. Those of skill in the art will know, or can readily ascertain, other substances which can act as suitable non-biologic and biologic drugs.

Bioactive molecules and biomolecules can be incorporated into the scaffold, or portion or component thereof, causing such to be imbedded within. Alternatively, chemical modification methods may be used to covalently link a molecule or biomolecule on the surface of the scaffold, or portion or component thereof. The surface functional groups of the scaffold, or portion or component thereof can be coupled with reactive functional groups of the molecules or biomolecules to form covalent bonds using coupling agents well known in the art such as aldehyde compounds, carbodiimides, and the like. Additionally, a spacer molecule can be used to gap the surface reactive groups and the reactive groups of the molecules or biomolecules to allow more flexibility of such molecules on the surface of the scaffold, or portion or component thereof. Other similar methods of attaching molecules or biomolecules to the interior or exterior of a scaffold, or portion or component thereof, will be known to one of skill in the art.

A scaffold 10 described herein can also be modified to incorporate a diagnostic agent, such as a radiopaque agent. The presence of such agents can allow a physician to monitor the progression of healing pr growth occurring internally. Such compounds include barium sulfate as well as various organic compounds containing iodine. Examples of these latter compounds include iocetamic acid, iodipamide, iodoxamate meglumine, iopanoic acid, as well as diatrizoate derivatives, such as diatrizoate sodium. Other contrast agents which can be utilized in the compositions of the application can be readily ascertained by those of skill in the art and may include the use of radiolabeled fatty acids or analogs thereof.

Concentration of an agent in a scaffold, or portion or component thereof, will vary with the nature of the compound, its physiological role, and desired therapeutic or diagnostic effect. A therapeutically effective amount is generally a sufficient concentration of therapeutic agent to display the desired effect without undue toxicity. A diagnostically effective amount is generally a concentration of diagnostic agent which is effective in allowing the monitoring of the integration of the scaffold, while minimizing potential toxicity. In any event, the desired concentration in a particular instance for a particular compound is readily ascertainable by one of skill in the art.

A scaffold, or portion or component thereof, can be enhanced, or strengthened, through the use of such supplements as human serum albumin (HSA), hydroxyethyl starch, dextran, or combinations thereof. The solubility of the scaffold materials or compositions therein can be enhanced by the addition of a nondenaturing nonionic detergent, such as polysorbate 80. Suitable concentrations of these compounds for use in the compositions of the application will be known to those of skill in the art, or can be readily ascertained without undue experimentation. Scaffold materials or compositions therein can be enhanced by the use of optional stabilizers or diluent. The proper use of these would be known to one of skill in the art, or can be readily ascertained without undue experimentation.

In some embodiments, the bioactive agent is released quickly from the scaffold 10 after implantation. In other embodiments, the bioactive agent can be formulated or bound to the scaffold 10 to be released slowly. For example, mineral coated microspheres can affect the release rate of a bioactive agent from a calcium phosphate coating, including building up layers of the coating with different dissolution patterns, or binding a component to the coating that provides a functional group to which the bioactive agent can be covalently bound. The agent can also be covalently or noncovalently bound to any region of the scaffold material itself to effect slow release, by any means known in the art.

Bioactive agents can be introduced into or onto the scaffold, or portion or component thereof, via a carrier based system, such as an encapsulation vehicle. For example, growth factors can be micro-encapsulated to provide for enhanced stability or prolonged delivery. Encapsulation vehicles include, but are not limited to, microparticles, liposomes, microspheres, or the like, or a combination of any of the above to provide the desired release profile in varying proportions. Other methods of controlled-release delivery of agents will be known to the skilled artisan. Moreover, these and other systems can be combined or modified to optimize the integration/release of agents within the scaffold 10.

Carrier based systems for incorporation of various agents into or onto the scaffold 10 can: provide for enhanced intracellular delivery; tailor biomolecule/agent release rates; increase or accelerate functional integration of layers; increase the proportion of agent that reaches its site of action; improve the transport of the agent to its site of action; allow co-localized deposition with other agents or excipients; improve the stability of the agent in vivo; prolong the residence time of the agent at its site of action by reducing clearance; decrease the nonspecific delivery of the agent to non-target tissues; decrease irritation caused by the agent; decrease toxicity due to high initial doses of the agent; alter the immunogenicity of the agent; decrease dosage frequency; or improve shelf life of the product.

Polymeric microspheres can be produced using naturally occurring or synthetic polymers and are particulate systems in the size range of 0.1 to 500 μm. Polymeric micelles and polymeromes are polymeric delivery vehicles with similar characteristics to microspheres and can also facilitate encapsulation and matrix integration of the agents described herein. Fabrication, encapsulation, and stabilization of microspheres for a variety of payloads are within the skill of the art (see e.g., Varde & Pack (2004) Expert Opin. Biol. 4(1) 35-51). Release rate of microspheres can be tailored by type of polymer, polymer molecular weight, copolymer composition, excipients added to the microsphere formulation, and microsphere size. Polymer materials useful for forming microspheres include PLA, PLGA, PLGA coated with DPPC, DPPC, DSPC, EVAc, gelatin, albumin, chitosan, dextran, DL-PLG, SDLMs, PEG (e.g., ProMaxx), sodium hyaluronate, diketopiperazine derivatives (e.g., Technosphere), calcium phosphate-PEG particles, and/or oligosaccharide derivative DPPG (e.g., Solidose). Encapsulation can be accomplished, for example, using a water/oil single emulsion method, a water-oil-water double emulsion method, or lyophilization. Several commercial encapsulation technologies are available (e.g., Prolease®, Alkerme).

Polymeric hydrogels can be used to integrate various agents into the scaffold 10. For example, a polymeric hydrogel including one or more agents can be introduced into pores of the scaffold 10.

"Smart" polymeric carriers can be used to integrate agents with the scaffold 10 (see generally, Stayton et al. (2005) Orthod Craniofacial Res 8, 219-225; Wu et al. (2005) Nature Biotech (2005) 23(9), 1137-1146). Carriers of this type utilize polymers that are hydrophilic and stealth-like at physiological pH, but become hydrophobic and membrane-destabilizing after uptake into the endosomal compartment (i.e., acidic stimuli from endosomal pH gradient) where they enhance the release of the cargo molecule into the cytoplasm. Design of the smart polymeric carrier can incorporate pH-sensing functionalities, hydrophobic membrane-destabilizing groups, versatile conjugation and/or complexation elements to allow the drug incorporation, and an optional cell targeting component. Polymeric carriers include, for example, the family of poly(alkylacrylic acid) polymers, specific examples including poly(methylacrylic acid), poly(ethylacrylic acid) (PEAA), poly(propylacrylic acid) (PPAA), and poly(butylacrylic acid) (PBAA), where the alkyl group is progressively increased by one methylene group. Various linker chemistries are available to provide degradable conjugation sites for proteins, nucleic acids, and/or targeting moieties. For example, pyridyl disulfide acrylate (PDSA) monomer allow efficient conjugation reactions through disulfide linkages that can be reduced in the cytoplasm after endosomal translocation of the agent(s).

Liposomes can be used to integrate agents with the scaffold 10. The agent carrying capacity and release rate of liposomes can depend on the lipid composition, size, charge, drug/lipid ratio, and method of delivery. Conventional liposomes are composed of neutral or anionic lipids (natural or synthetic). Commonly used lipids are lecithins such as (phosphatidylcholines), phosphatidylethanolamines (PE), sphingomyelins, phosphatidylserines, phosphatidylglycerols (PG), and phosphatidylinositols (PI). Liposome encapsulation methods are commonly known in the arts (Galovic et al. (2002) Eur. J. Pharm. Sci. 15, 441-448; Wagner et al. (2002) J. Liposome Res. 12, 259-270). Targeted liposomes and reactive liposomes can also be used in combination with the agents and matrix. Targeted liposomes have targeting ligands, such as monoclonal antibodies or lectins, attached to their surface, allowing interaction with specific receptors and/or cell types. Reactive or polymorphic liposomes include a wide range of liposomes, the common property of which is their tendency to change their phase and structure upon a particular interaction (e.g., pH-sensitive liposomes) (see e.g., Lasic (1997) Liposomes in Gene Delivery, CRC Press, FL).

Toxicity and therapeutic efficacy of agents discussed herein can be determined by standard pharmaceutical procedures in cell cultures and/or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where large therapeutic indices are preferred.

Manufacture

In various aspects of the application, biocompatible scaffold materials are fabricated into modules 30 or racks 20 as described above. Fabrication of biocompatible scaffold materials into shaped 3-dimensional scaffold components, such as a module 30 or a rack 20, can be according to a variety of methods known to the art. Scaffolds 10 can be prepared according to methods described in U.S. Pat Pub No. 2003/0069718, U.S. Pat Pub No. 2006/0276925, U.S. Pat Pub No. 2008/0195211, or U.S. Pat Pub No. 2008/0215093, each incorporated herein by reference.

Scaffold synthesis techniques include, but are not limited to, nanofiber self-assembly (e.g., hydrogel scaffolds), textile technologies (e.g., non-woven polyglycolide structures), solvent casting and particulate leaching, gas foaming, emulsification/freeze-drying, thermally induced phase separation, CAD/CAM technologies, or a combination of these techniques. For example, biocompatible scaffold materials can be fabricated into a shaped 3-dimensional module 30 or rack 20 via computer aided design/manufacturing (CAD/CAM) technologies.

Figure 4:
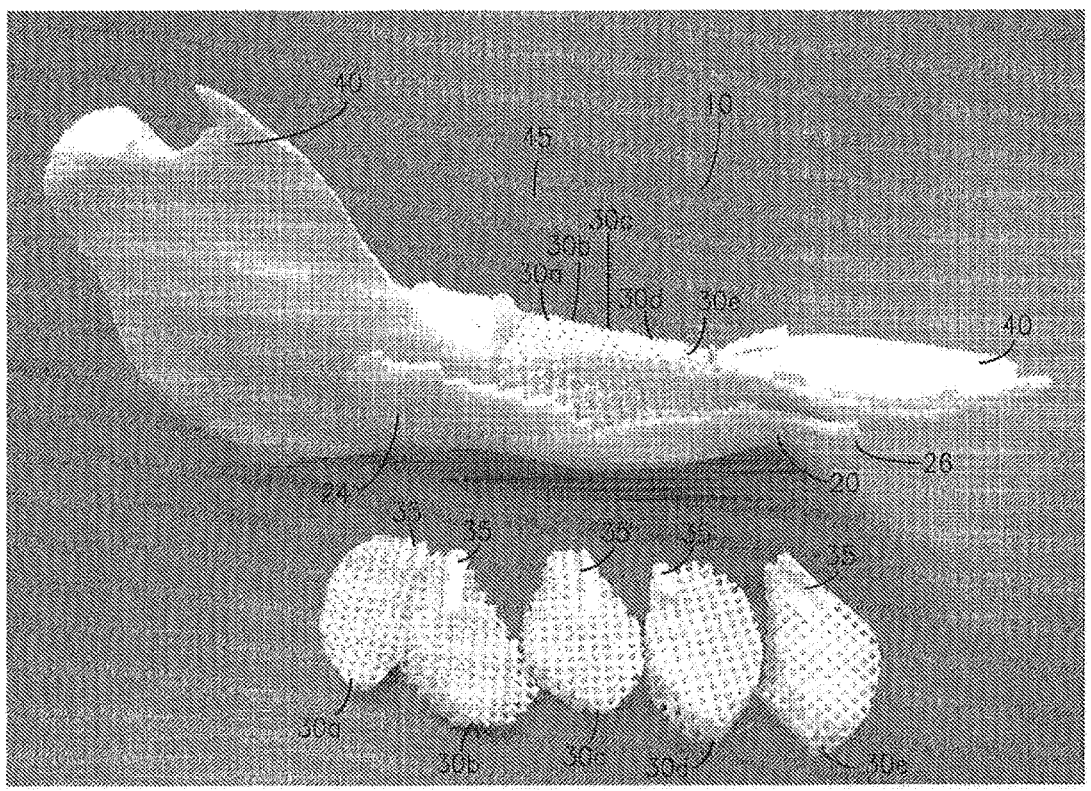
FIG. 4 is an image showing a modular scaffold made from a degradable polymer using a laser sintering techniques. Modules are placed in the scaffold in the upper portion of the image and laid out individually in the lower portion of the image.

A scaffold, or portion or component thereof, described herein can be manufactured using a range of solid free-form fabrication techniques including, but not limited to, laser sintering. Another method of manufacturing a scaffold, or portion or component thereof, described herein is a molding process. A scaffold, a module 30, a rack 20, or a sleeve can be manufactured individually. An exemplary modular mandible scaffold 10 manufactured from a degradable polymer polycaprolactone is depicted in FIG. 4.

In CAD/CAM technologies of scaffold fabrication, first a three-dimensional structure is designed using computer aided design (CAD) software and then the scaffold 10 is generated by computer aided manufacture (CAM) process. CAM processes for scaffold fabrication include, for example, using ink-jet printing of polymer powders (e.g., Bioplotter, Envisiontec, Gladbeck, Germany) or through rapid prototyping technology such as fused deposition modeling (FDM). Scaffold fabrication using a bioplotter, or similar device, provides the advantage of co-deposition of live cells (e.g., stem cells and other cells described herein). For example, multiple printing/deposition heads can be used in the fabrication of materials, co-deposition of cells, and/or addition of agents such as growth factors and the like so as to provide for a fabricated scaffold 10 with internal porosity features and seeded cells or additional agents within the scaffold material or its pores.

Scaffold fabrication via CAD/CAM technologies can employ 3-dimensional data of the target hard tissue. As described above, the image data can be obtained from a subject's own tissue or from similar tissue from other than the subject. Software can import 3-dimensional volume data and generate a plotting pathway for deposition of the scaffold material. For example, dxf-data can be prepared by processing CT scanned images or obtained from medical CAD programs like VOXIM or MIMICS, which reconstructs a 3D model from DICOM images. The 3-dimensional model can be an integral solid of which body surrounded by surface objects. Once a 3-dimensional volume data file (e.g., a dxf file) is constructed, the size, alignment, and position is adjusted per the dispensing layouts and channel configurations. Such adjustment is within the ordinary skill in the art. In a typical procedure, a selected scaffold polymer material is placed inside the container of the dispensing module 30, and the module 30 heated to a pre-optimized temperature to keep the polymer melted with appropriate viscosity for dispensing. The polymer solution can also be prepared using a solvent. With solvent, the desired viscosity can be controlled by concentration of solute, and in some embodiments, no heat is required. The polymer solution can be dispensed in air or in liquid, optionally with chemicals required for solidification. For example, melted PCL can be dispensed in air.

For CAM fabrication techniques, the pore size of the resulting scaffold 10 can be determined by distance between strands. The strand size can be determined by, for example, viscosity of solution, needle inner diameter, and dispensing speed. Preferably, pore size parameters are determined prior to fabrication of a 3-dimensional structure, as is within the skill of the art.

Use

Various embodiments of the scaffolds 10 described herein hold significant clinical value because of their modular design, biomaterials, anatomic shape, and interior structural features. Various scaffolds 10 of the present disclosure can provide multiple modular inserts of all degradable materials along with optional incorporation of cells, osteoinductive coatings, or release of bioactive agents. It is these features, at least in part, which sets the tissue modules 30 disclosed herein apart from other conventional tissue defect treatment options.

Another provided aspect is a method of treating a tissue defect in a subject by implanting a tissue scaffold 10 described herein into a subject in need thereof. A determination of the need for treatment will typically be assessed by a history and physical exam consistent with the tissue defect at issue. Subjects with an identified need of therapy include those with a diagnosed tissue defect. The subject is preferably an animal, including, but not limited to, mammals, reptiles, and avians, more preferably horses, cows, dogs, cats, sheep, pigs, and chickens, and most preferably human.

As an example, a subject in need may have damage to a tissue, and the method provides an increase in biological function of the tissue by at least 5%, 10%, 25%, 50%, 75%, 90%, 100%, or 200%, or even by as much as 300%, 400%, or 500%. As yet another example, the subject in need may have a disease, disorder, or condition, and the method provides an engineered tissue scaffold 10 sufficient to ameliorate or stabilize the disease, disorder, or condition. For example, the subject may have a disease, disorder, or condition that results in the loss, atrophy, dysfunction, or death of cells. Exemplary treated conditions include arthritis; osteoarthritis; osteoporosis; osteochondrosis; osteochondritis; osteogenesis imperfecta; osteomyelitis; osteophytes (i.e., bone spurs); achondroplasia; costochondritis; chondroma; chondrosarcoma; herniated disk; Klippel-Feil syndrome; osteitis deformans; osteitis fibrosa cystica, a congenital defect that results in the absence of a tissue; accidental tissue defect or damage such as fracture, wound, or joint trauma; an autoimmune disorder; diabetes (e.g., Charcot foot); cancer; a disease, disorder, or condition that requires the removal of a tissue (e.g., tumor resection); and/or a disease, disorder, or condition that affects the trabecular to cortical bone ratio. For example, a modular tissue scaffold 10 described herein can be implanted in a subject who would otherwise need to undergo an osteochondral autograft. In a further example, the subject in need may have an increased risk of developing a disease, disorder, or condition that is delayed or prevented by the method.

Implantation of a tissue scaffold 10 described herein is within the skill of the art. For example, a scaffold rack 20 can be fixed to a tissue site flanking or surrounding a defect using a range of surgical fixation techniques including, but not limited to, degradable fixation pins sonically welded through the fixation sleeve or post into the surrounding tissue to form a bond; a metal screw fixation where screws are used to fix the mesh; or a degradable screw fixation where screws are used to fix the mesh.

A scaffold 10 described can be coupled with or attached to tissue, directly or indirectly, including, but not limited to, using screws, welding, press or snap fit, or fasteners, such as, for example, made of metal, plastic or some other material. Means such as a central pin, screw, or rod in a tunnel can be used to connect a scaffold, or components thereof, into a tissue, such as bone 40. As another example, a key that can be expanded can join the scaffold 10 and a tissue, such as bone 40. As other examples, a scaffold 10 and a tissue can be joined in situ according to welding, UV, glue, or thermosetting. A scaffold 10 described herein can be anchored to other tissues, such as ligaments. Welding can be accomplished by the application of energy, such as, for example, heat, ultrasonic or some other method.

The scaffold 10 assembly can be either fully or partially implanted into a tissue of the subject to become a functioning part thereof. The scaffold 10 can initially attaches to and communicates with the host through a cellular monolayer. In some embodiments, over time, the introduced cells (where present) can expand and migrate out of the polymeric scaffold material matrix to the surrounding tissue. After implantation, cells surrounding the tissue scaffold 10 can enter through cell migration. The cells surrounding the tissue module 30 can be attracted by biologically active materials, including biological response modifiers, such as polysaccharides, proteins, peptides, genes, antigens, and antibodies which can be selectively incorporated into the matrix to provide the needed selectivity, for example, to tether the cell receptors to the scaffold 10 or stimulate cell migration into the scaffold, or both. Generally, the scaffold material is porous, allowing for cell migration, augmented by both biological and physical-chemical gradients. One of skill in the art will recognize and know how to use other biologically active materials that are appropriate for attracting cells to the matrix.

The methods, compositions, and devices of the application can include concurrent or sequential treatment with one or more of enzymes, ions, growth factors, and biologic agents, such as thrombin and calcium, or combinations thereof. The methods, compositions, and devices of the application can include concurrent or sequential treatment with non-biologic and/or biologic drugs.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

This example describes implantation of a bioresorbable PCL scaffold, resorbable CaP coating, and coated resorbable PCL fixation pins.

Figure 5A:
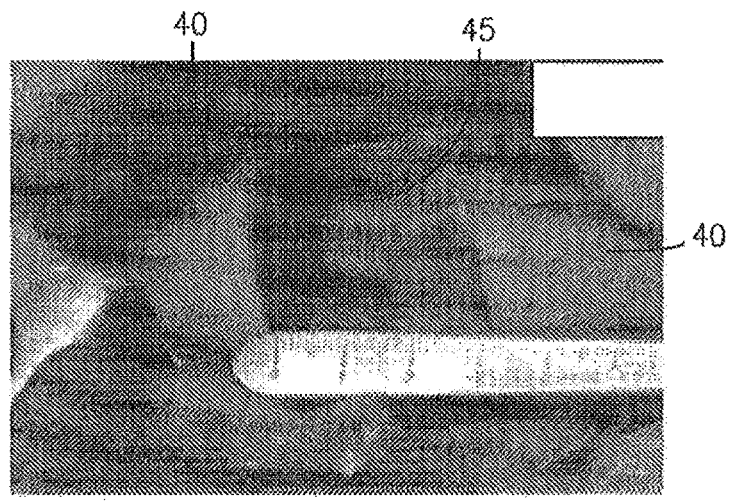
FIGS. 5A-C are a series of photographs showing creation of a surgical defect, bioresorbable pin placement, and complete welded scaffold in an adult Yorkshire pig model.
Figure 5B:
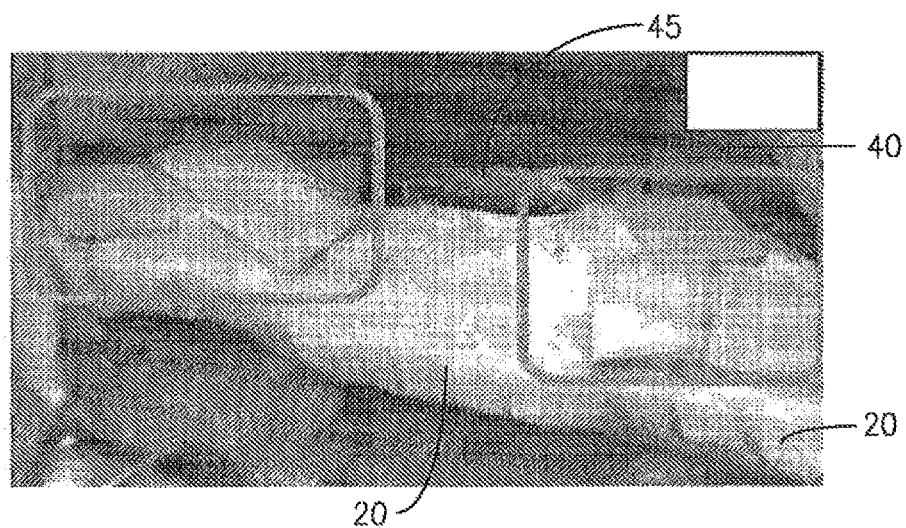
Figure 5C:
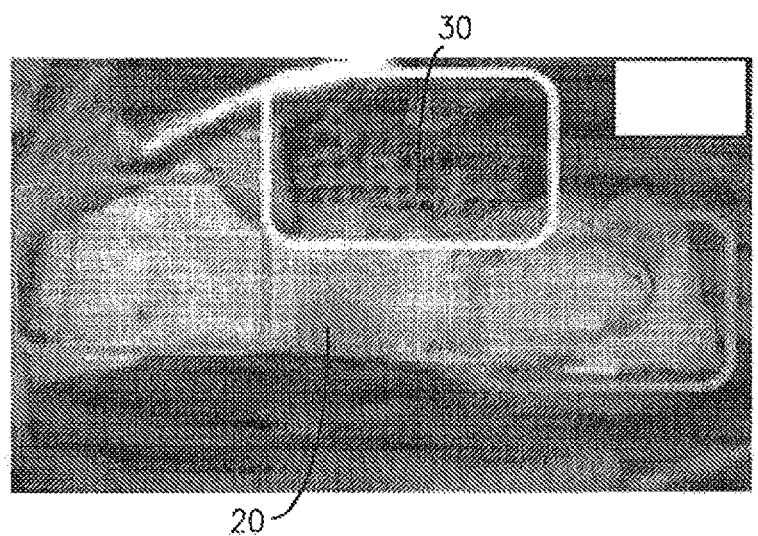

A 3.5 cm mandibular segmental defect was surgically created in a an adult Yorkshire pig model (see FIG. 5A). Initial sizing of scaffold sleeve with pins (blue circle) located in drill holes is shown in FIG. 5B (rectangular highlights on left and right of image). A complete welded scaffold bioresorbable pins were implanted in the surgical defect of the adult Yorkshire pig model. Final scaffold implantation and welding of modules (rectangular highlight in upper center of image) and welding of pins (rectangular highlights on left and right of image) are shown in FIG. 5C. The modules shown in FIG. 5C may be mechanically integrated by ultrasonic means, thermal welding, or gluing. Mechanically integrating the modules increases the interface strength between the first module and the second module.

Figure 6A:
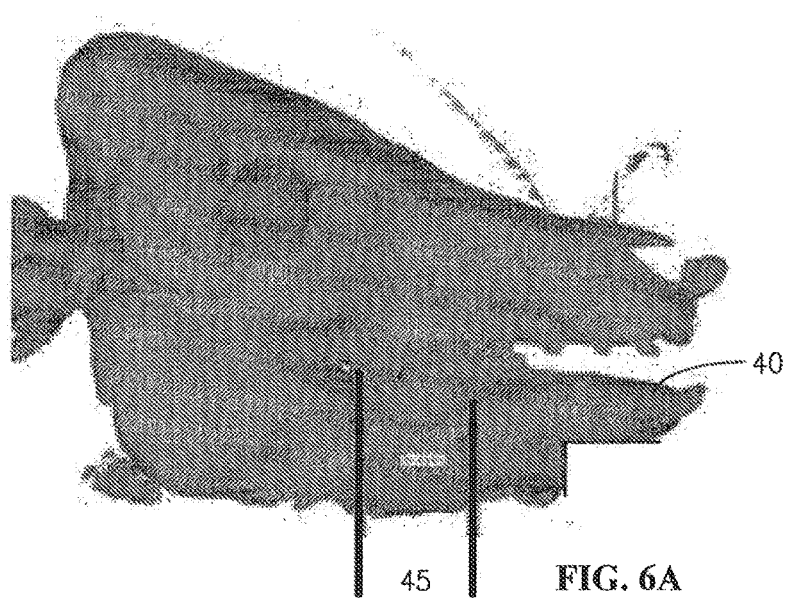
FIGS. 6A-C are a series of images showing bone fill and correct anatomic shape of an implanted scaffold at 6 months in vivo.
Figure 6B:
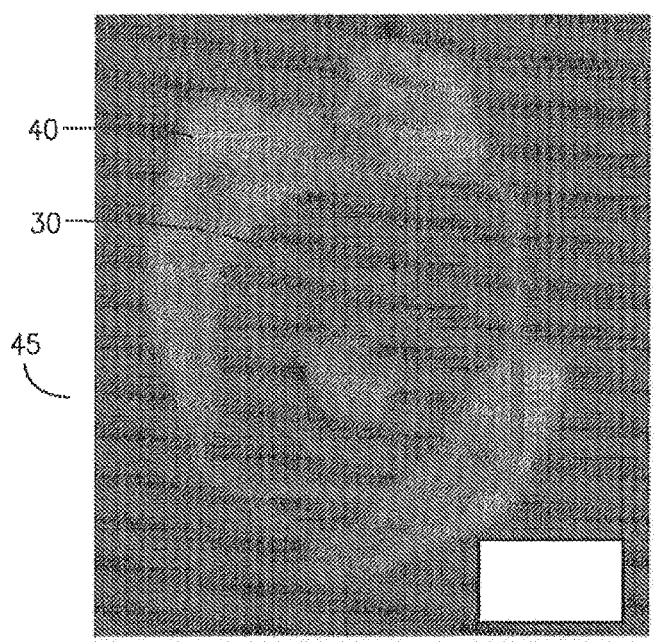
Figure 6C:
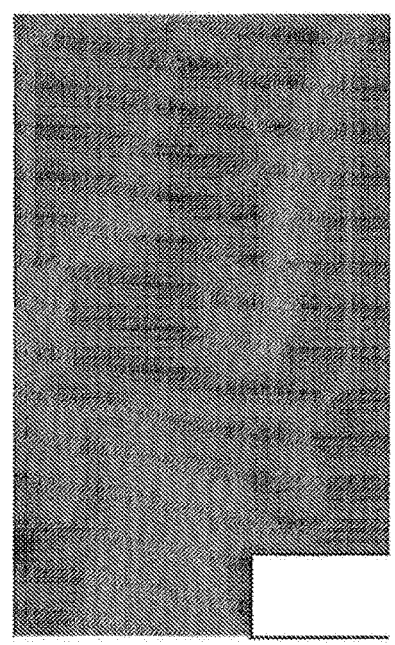

Results showed that 7 months post-surgery, the pigs receiving the implants retained complete masticatory function, being able to eat a normal diet. CT scans of pigs at 6 months post-surgery show that the scaffolds support masticatory loads and allow bone 40 formation with bridging of the defect and some bone 40 fill in the scaffold (see e.g., FIGS. 6A-C). Three dimensional reconstruction in FIG. 6A shows bone 40 bridging the original defect (defect margins shown by vertical lines). As seen in FIG. 6A, the mandible after 6 months is in a correct anatomic position. Pore structure and bone 40 growth in the scaffold module is shown in FIG. 6B (rectangular highlight). Bone 40 fill in a second pig implanted with the scaffold is shown in FIG. 6C (rectangular highlight).

This demonstrates that the completely resorbable scaffold with resorbable fixation can withstand in vivo mastication loads without failure.

Figure 7A:
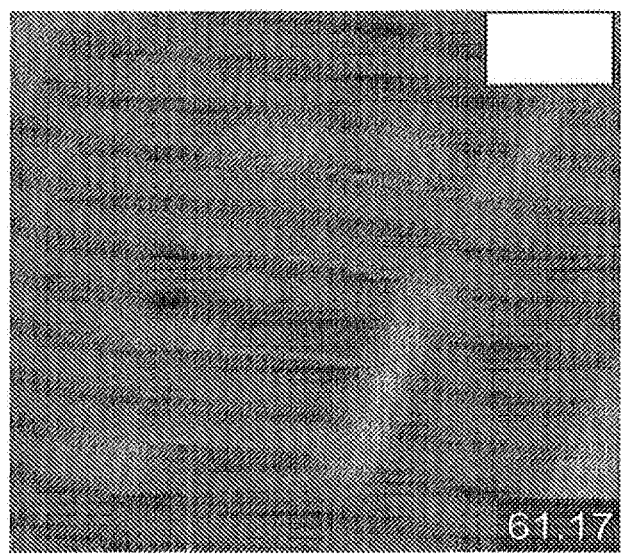
FIGS. 7A-B are a pair of images showing bioresorbable pin fixation after 6 months in vivo.
Figure 7B:
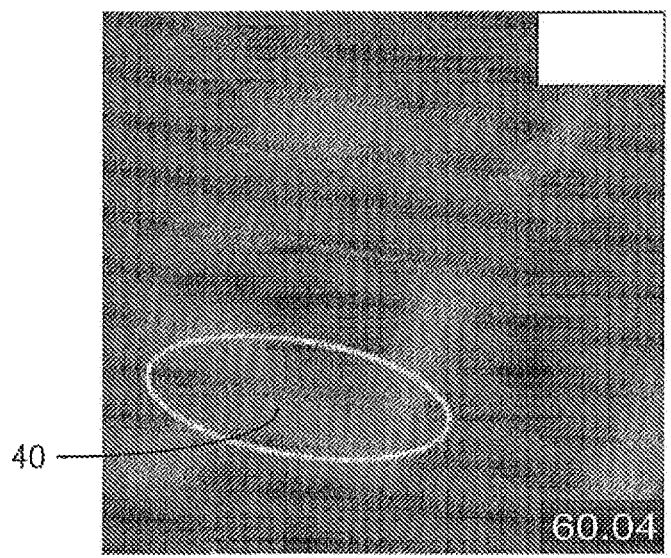

Bioresorbable pin fixation in vivo after 6 months post-surgery are shown in FIGS. 7A-B. Dual pin tracts in mandible are shown in FIG. 7A (tracts outlined with solid line). FIG. 7B is a slice image 1.2 mm from the view in FIG. 7A, showing bone 40 formation (circular highlight) underneath the lower pin tract.

The above data validates an embodiment of a platform resorbable mandibular reconstruction system. First, the modular platform system welded in the OR has sufficient strength to withstand masticatory loads, and it maintained fixation to the mandible, allowing the pigs to masticate normally. Second, the scaffolds support bone 40 formation even in the absence of a biologic. It is presently expected that addition of a an osteobiologic can result in even more rapid and complete bone 40 regeneration.

Example 2

This example describes design and implantation of a modular scaffold for placement of a modular mandibular reconstruction scaffold within a mandibular defect in a pig mandible.

Figure 8:
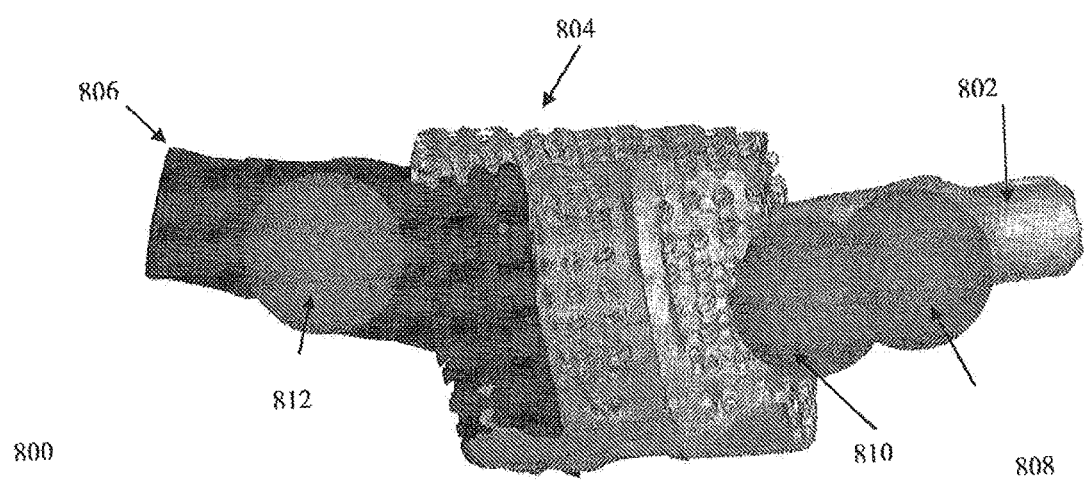
FIG. 8 shows a medial-lateral view of a modular scaffold design with marrow space interfaces that mechanically stabilize the endoprosthesis in addition to pins that are placed through the marrow space interfaces.

FIG. 8 shows a medial-lateral view of a modular scaffold design 800 with marrow space interfaces that mechanically stabilize the endoprosthesis in addition to pins that are placed through the marrow space interfaces. Three modules 802, 804, and 806 are shown in FIG. 8 with pins 808, 810, and 812 providing additional fixation. The modules 802, 804, and 806 interface with cut bone ends protruding into the marrow space. The pins 808, 810, and 812 provide additional fixation for the scaffold modules.

Figure 9:
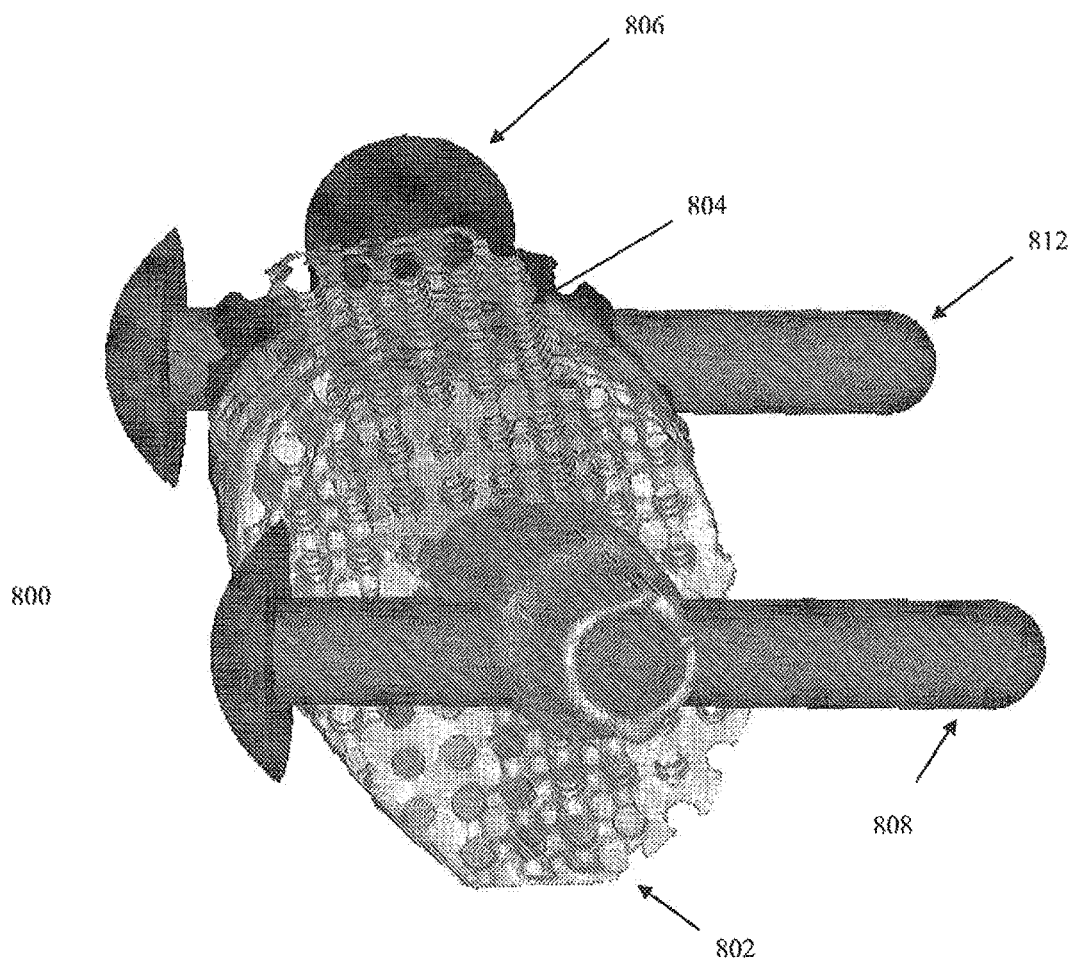
FIG. 9 shows an anterior-posterior view of the modular scaffold design from FIG. 8 with associated pins.

FIG. 9 shows an anterior-posterior view of modular scaffold design 800 from FIG. 8 with associated pins. The anterior-posterior view of modular scaffold design 800 shows scaffolds 802 and 804, and associated pins 808 and 812.

Figure 10:
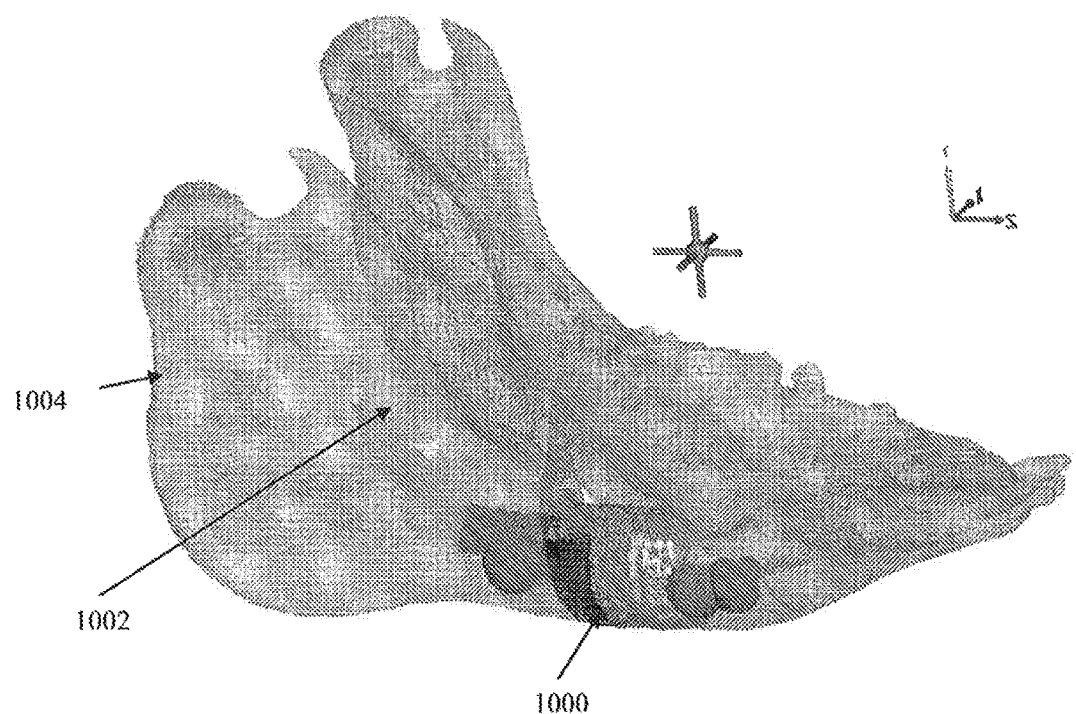
FIG. 10 shows placement of a modular mandibular reconstruction scaffold based on the designs shown in FIGS. 8 and 9 within a mandibular defect in a pig mandible.

FIG. 10 shows placement of a modular mandibular reconstruction scaffold 1000 corresponding to modular scaffold design 800 within a mandibular defect 1002 in a pig mandible 1004. This illustration shows how the modular scaffold stabilizes the mandibular defect and interfaces with the marrow space of the mandible.

REFERENCES

Hollister, S. J. Scaffold engineering: a bridge to where? Biofabrication 1:012001 (2009).

Lin et al. "A novel method for internal architecture design to match bone elastic properties with desired porosity", Journal of Biomechanics 37:623-36, 2004.

Murphy et al., "Bioinspired growth of crystalline carbonate apatite on biodegradable polymer substrata", J Am Chem Soc 124:1910-7, 2002.

Murphy et al., "Effects of a bone-like mineral film on phenotype of adult human mesenchymal stem cells in vitro", Biomaterials 26:303-10, 2005.

The invention claimed is:

1. A biocompatible scaffold system for filling a tissue gap comprising:
a tissue scaffold comprising
a plurality of porous and biodegradable modules, wherein each of the plurality of porous and biodegradable modules is comprised of a biodegradable polymer material and defines an irregular disk shape having a first side and a second side opposite the first side, wherein each of the plurality of porous and biodegradable modules is configured to connect to another of the plurality of porous and biodegradable modules; and,
a biodegradable tissue scaffold rack comprising a biodegradable polymer material, wherein the tissue scaffold rack defines a proximal end and a distal end and is configured to span a tissue gap in a mammal between the proximal end and the distal end, the tissue scaffold rack defining a trough shaped portion having at least two side regions and a bottom region;
wherein at least one module connector is disposed at the bottom region of the tissue scaffold rack; and,
wherein each of the plurality of porous and biodegradable modules is configured to fit into and connect with the biodegradable tissue scaffold rack by contacting the bottom region and substantially spanning the two side regions.

2. The scaffold system of claim 1, further comprising a fixation device configured to couple the tissue scaffold to tissue adjacent to the tissue gap.

3. The scaffold system of claim 2, wherein the fixation device includes one or more of a screw, a pin, or a rod.

4. The scaffold system of claim 3, wherein the fixation device comprises metal.

5. The scaffold system of claim 2, wherein the fixation device comprises a degradable material.

6. The scaffold system of claim 1, wherein a first module of the plurality of porous and biodegradable modules is configured to connect to a second module of the plurality of porous and biodegradable modules through melt fusion of the second side of the first module to the first side of the second module.

7. The scaffold system of claim 1, wherein the at least one module connector is configured to connect with the plurality of porous and biodegradable modules.

8. The scaffold system of claim 7, wherein at least one of the plurality of porous and biodegradable modules comprises a rack connector configured to connect with the at least one module connector of the tissue scaffold rack.

9. The scaffold system of claim 8, wherein the rack connector is configured to mechanically couple to the module connector.

10. The scaffold system of claim 9, wherein the module connector is a recess and the rack connector is a protuberance that is configured to fit into the recess.

11. The scaffold system of claim 9, wherein the rack connector is a recess and the module connector is a protuberance that is configured to fit into the recess.

12. The scaffold system of claim 9, wherein the module connector and the rack connector are configured as a snap fit, mortise and tenon, or dovetail connection.

13. The scaffold system of claim 1, wherein a first module of the plurality of porous and biodegradable modules includes a connector on the first or second side of the module, and a second module of the plurality of porous and biodegradable modules includes a complementary connector on the first or second side of the module, wherein the complementary connector is configured to couple with the connector of the first module.

14. The scaffold system of claim 13, wherein the first module connector and the second module complementary connector are configured to mechanically connect.

15. The scaffold system of claim 13, wherein the first module connector and the second module complementary connector are configured to melt fuse.

16. The scaffold system of claim 1, wherein the irregular disk shape corresponds to an outline of a portion of the tissue gap.

17. The scaffold system of claim 1, wherein the plurality of porous and biodegradable modules further comprise a crystalline or mineral component.

18. The scaffold system of claim 17, wherein the plurality of porous and biodegradable modules comprise a composite mixture of the biodegradable polymer material and the crystalline or mineral component.

19. The scaffold system of claim 17, wherein the biodegradable polymer material comprises polycaprolactone.

20. The scaffold system of claim 17, wherein the degradable polymer material comprises polycaprolactone and the crystalline or mineral component includes calcium and phosphate.

21. The scaffold system of claim 1, further comprising a bioactive agent.

22. The scaffold system of claim 21, wherein the bioactive agent includes an antibiotic.

23. The scaffold system of claim 21, wherein the bioactive agent includes bone morphogenetic protein (BMP), demineralized bone matrix, bone marrow aspirate, transforming growth factor, fibroblast growth factor, insulin-like growth factor, platelet derived growth factor, vascular endothelial growth factor, growth and development factor-5, or platelet rich plasma, or a mixture thereof.

24. The biocompatible system of claim 1, further comprising an isolated vertebrate cell.

\* \* \* \* \*